United States Patent [19]
Hoxie

[11] Patent Number: 5,994,515
[45] Date of Patent: Nov. 30, 1999

[54] ANTIBODIES DIRECTED AGAINST CELLULAR CORECEPTORS FOR HUMAN IMMUNODEFICIENCY VIRUS AND METHODS OF USING THE SAME

[75] Inventor: James A. Hoxie, Berwyn, Pa.

[73] Assignee: Trustees of the University of Pennsylvania, Philadelphia, Pa.

[21] Appl. No.: 08/882,435

[22] Filed: Jun. 25, 1997

Related U.S. Application Data

[60] Provisional application No. 60/020,396, Jun. 25, 1996, and provisional application No. 60/020,647, Jun. 27, 1996.

[51] Int. Cl.$^6$ .................................................. C07K 16/28
[52] U.S. Cl. ................................ 530/388.22; 530/387.1; 530/389.1; 424/143.1; 424/144.1
[58] Field of Search ........................ 530/387.1, 388.1, 530/388.15, 388.21, 388.22, 388.3, 388.35, 389.1; 424/131.1, 137.1, 141.1, 142.1, 143.1, 144.1

[56] References Cited

PUBLICATIONS

Hoxie, et al. : Biological characterization of a Simian . . . : J. Vir. : pp. 2557–2568, Aug. 1988.
Feng, et al. : HIV–1 Entry Cofactor: functional cDNA . . . : Science: vol. 272: pp. 872–877, May 1996.
Cohen: Likely HIV cofactor Found: Science: vol. 272: pp. 809–810, May 1996.
Alkhatib et al., 1996, *Science* 272:1955–1958.
Berson et al., 1996, *J. Virol.* 70:6288–6295.
Bleul et al., 1996, *Nature* 282:829–833.
Bleul et al., 1997, *Proc. Natl. Acad. Sci. USA* 94:1925–1930.
Brass et al., 1994, *J. Biol. Chem.* 269:2943–2952.
Brelot et al., 1997, J. Virol. 71:4744–4751.
Burton et al., 1994, *Adv. Immunol.* 57:191–280.
Chaudhuri et al. , 1994, *J. Biol. Chem.* 269:7835–7838.
Chesebro et al., 1990, *J. Virol.* 64:215–221.
Choe et al., 1996, *Cell* 85:1135–1148.
Clackson et al., 1991, *Nature* 352:624.
Clapham et al., 1992, *J. Virol.* 66:3531–3537.
Clapham, 1991, *Rev. in Med. Virol.* 1:51–58.
Clapham et al., 1991, *Virology* 181:703–715.
Clapham et al., 1987, *Virology* 158:44–51.
Cocchi et al., 1995, *Science* 270:1811–1815.
Cohen, 1996, *Science* vol. 272:809–810.
Collins, "Scientists make AIDS breakthrough", *The Philadelphia Inquirer* (Jun. 20, 1996 ed.).
Crise et al., 1990, *J. Virol.* 64:5585–5593.
Deng et al., 1996, *Nature* 381:661–666.
Doranz et al., 1996, *Cell* 85:1149–1158.
Dragic et al., 1996, *Nature* 381:667–673.
Dragic et al., 1995, *J. Virol.* 69:1013–1018.
D'Souza et al., 1996, "Chemokines and HIV–1 second receptors", *Nature Medicine* 2:1293–1300.
Earl et al., 1994, *J. Virol.* 68:3015–3026.
Endres et al., 1996, "CD4–Independent Infection by HIV–2 Is Mediated by Fusin CXCR4", *Cell* 87:745–756.
Fahey et al., 1992, *Clin. exp. Immunol.*, 88: 1–5.
Fauci et al., 1996, *Nature* 384:529–534.
Feng et al., 1996, "HIV–1 Entry Cofactor: Functional cDNA Cloning of a Seven–Transmembrance, G Protein–Coupled Receptor", *Science* 272:872–876.
Fox 1994, No Winners Against AIDS, *Bio/Technology*, vol. 12: p. 128.
Harlow et al. 1988, In: *Antibodies, A Laboratory Manual*, Cold Spring Harbor, NY—too voluminous to submit.
Harouse et al., 1991, *Science* 253:320–323.
Haynes et al., 1996, The Finnish Medical Society DUODECIM, *Ann Med'* 28:39–41.
Hesselgesser et al., 1997, "CD–4–independent association between HIV–1 gp 120 and CXCR4: functional chemokine receptors are expressed in human neurons", *Current Biology* 7:112–121.
Hoxie et al., 1988, *J. Virol.* 62:2557–2568.
Hoxie et al., 1986, *Science* 234:1123–1127.
Ikeuchi et al., 1990, *J. Virol.* 64:226–4231.
Jonker et al., 1993, "In vivo treatment with a monoclonal chimeric anti–CD4 antibody results in prolonged depletion of circulating CD4+ cells in chimpanzees", *Clin. Exp. Immunol.* 93:301–307.
Koot et al., 1992, *AIDS* 6:49–54.
LaBranche et al., 1994, *J. Virol.* 68:5509–5522.
Lapham et al., 1996, *Science* 274:602–605.
Leung et al., 1994, "Chimerization of LL2, a Rapidly Internalizing Antibody Specific for B Cell Lymphoma", *Hybridoma* 13:469–476.
Li et al., 1990, *J. Virol.* 64:1383–1387.
LoBuglio et al., 1989, "Mouse/human chimeric monoclonal antibody inman: Kinetics and immune response". *Proc. Natl. Acad. Sci.* USA 86:4220–4224.
Lu et al., 1997, *Proc. Natl. Acad. Sci. USA*, vol. 94:6426–6431.
Maddon et al., 1986, *Cell* 47:333–348.
McDougal et al., 1986, *Science* 231:382–385.
McKnight et al., 1997 "Inhibitionof Human Immunodeficiency Virus Fusion by a Monoclonal Antibody to a Coreceptor (CXCR4) is both Cell Type and Virus Strain Dependent", *J. Virol.* 71:1692–1696.
McKnight et al., 1996, J. Virol. 70:4598–4606.
McKnight et al., 1995, *J. Virol.* 69:3167–3170.
McKnight et al., 1994, *Virology*, 201:8–18.
Miyoshi et al., 1981 *Nature*, 294:770–771.
Moore, 1997, *Science* 276:51.
Nara et al., 1988, *Nature* 332:469–470.
Nara et al., 1987, *AIDS Res. and Hum. Retroviruses* 3:283–202.
Neote et al., 1993, *Cell* 72:415–425.
Oberlin et al., 1996, *Nature* 382:833–835.
Pelchen–Matthews et al., 1989, *EMBO J.* 8:3641–3649.
Picard et al., 1997, *Virology*, 231:105–111.

(List continued on next page.)

*Primary Examiner*—Robert D. Budens
*Attorney, Agent, or Firm*—Akin, Gump, Strauss, Hauer & Feld, L.L.P.

[57] ABSTRACT

The invention relates to an anti-immunodeficiency virus antibody which binds to a cellular protein and diagnostic and therapuetic methods of using the same.

9 Claims, 14 Drawing Sheets

OTHER PUBLICATIONS

Power et al., 1996, *Trends Pharmacol. Sci.* 17:209–213.
Power et al., 1995, *J. Biol. Chem.* 270:19495–19500.
Premack et al., 1996, "Chemokine receptors: Gatways to inflammation and infection", *Nature Medicine* 2:1174–1178.
Queen et al., 1989. *Poc. Natl. Acad. Sci USA,* vol. 86:10029–10033.
Ratner et al., 1987, *AIDS Res. and Hum. Retroviruses* 3:57–69.
Sambrook et al., 1989, *Molecular Cloning: A Laboratory Manual,* Cold Spring Harbor, NY—too voluminous to submit.
Samson et al., 1996, *Biochemistry* 35:3362–3367.
Sattentau, et al., 1986, Epitopes of the CD4 Antigen and HIV Infection, *Science,* vol. 234:1120–1122.
Schneider–Schaulies et al., 1995, *Proc. Natl. Acad. Sci. USA* 92:3943–3947.
Simmons et al., 1996, *Virology* 70:8355–8360.
Simmons et al., 1995, *Virology* 209:696–700.
Stefano et al., 1993, *J. Virol.* 67:6707–6715.
Striziki et al., 1997. *J. Virol.* p. 5678–5683.
Sung Co et al., 1992, "Chimeric and Humanized Antibodies with Specificity for the CD33 Antigen", *J. Immunol.* 148:1149–1154.
Takeuchi et al., 1991, *J. Virol.* 65:1710–1718.
Tateno et al., 1989, *Proc. Natl. Acad. Sci. USA* 86:4287–4290.
Weiner et al., 1991, *Pathobiol.* 59:361–371.
Willett et al., 1997, "Common mechanism of infection by lentiviruses", *Nature* 385:587.
Weiss et al., 1996, *Nature* 381:647–648.
Wright et al., 1992, "Genetically Engineered Antibodies: Progress and Prospects", *Critical Rev. in Immunol.* 12(3, 4):125–168.
Wu et al., 1996, *Nature* 384:179–183.
Zagury et al., 1988, *Proc. Natl. Acad. Sci. USA* 85:5941–5945.

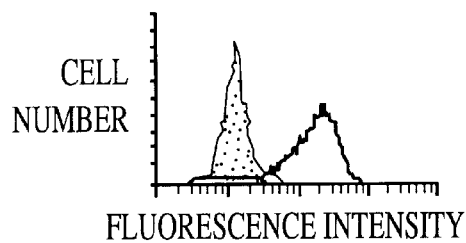
FIG. 1Ai
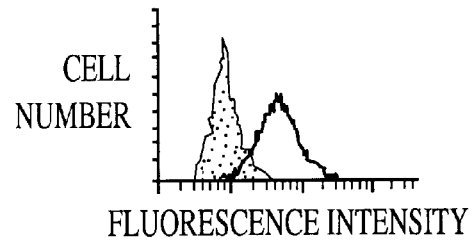
FIG. 1Aii
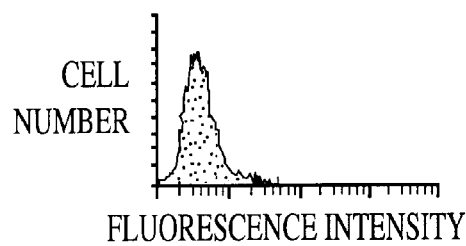
FIG. 1Aiii
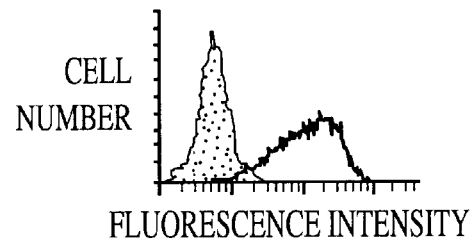
FIG. 1Aiv
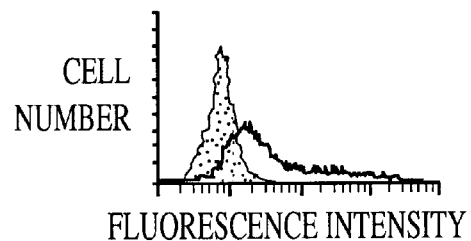
FIG. 1Av
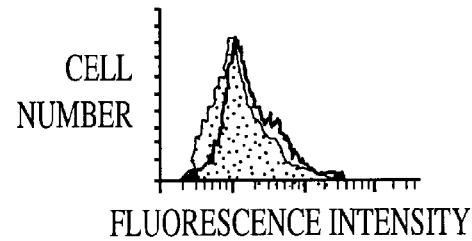
FIG. 1Avi

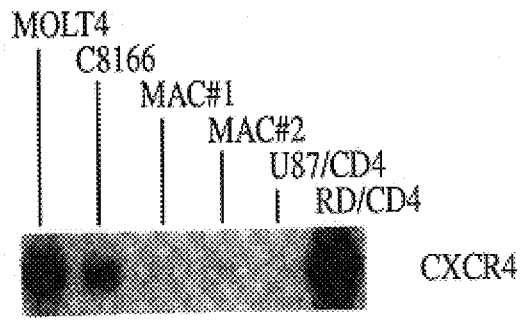
FIG. 1Bi
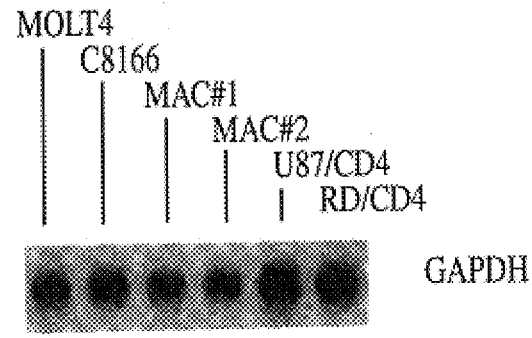
FIG. 1Bii
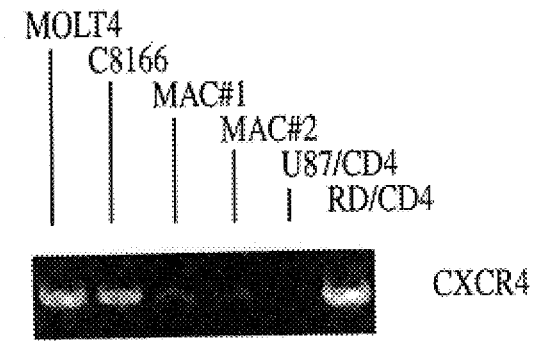
FIG. 1Ci
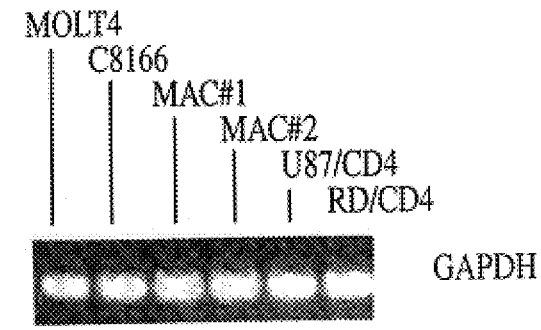
FIG. 1Cii

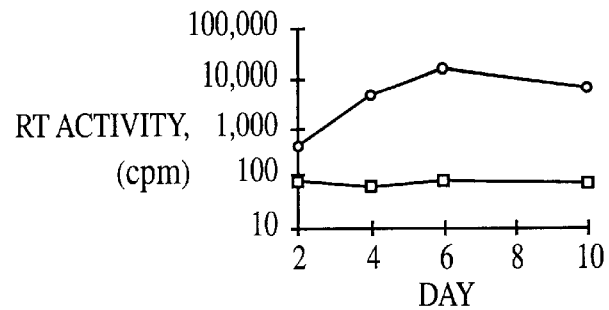
FIG. 3Ai
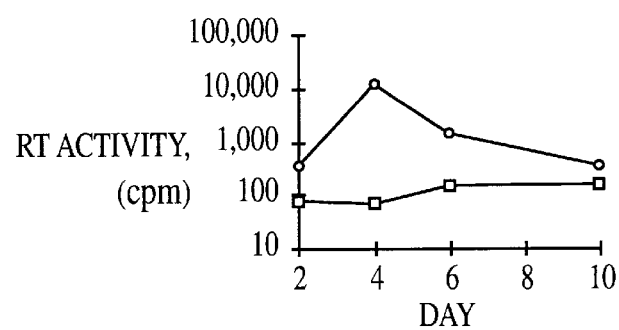
FIG. 3Aii
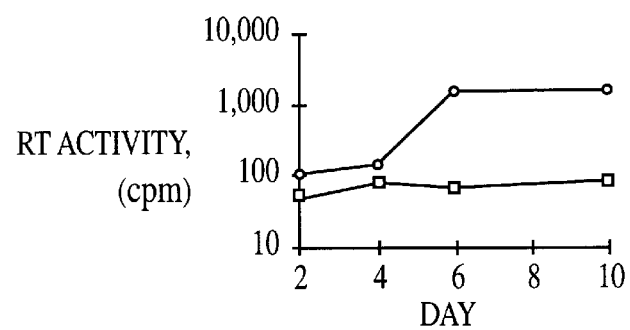
FIG. 3Aiii
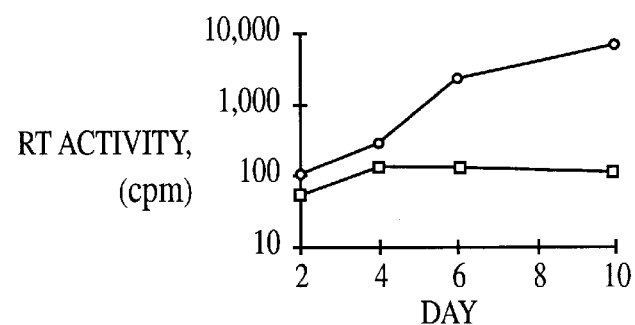
FIG. 3Aiv

FIG. 3Avi

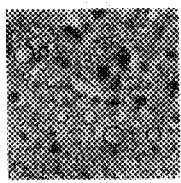 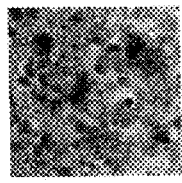 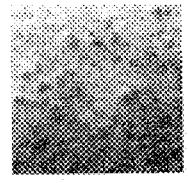 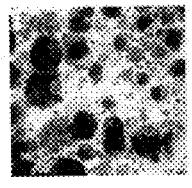 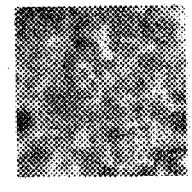
FIG. 3Ci    FIG. 3Cii    FIG. 3Ciii    FIG. 3Civ    FIG. 3Cv

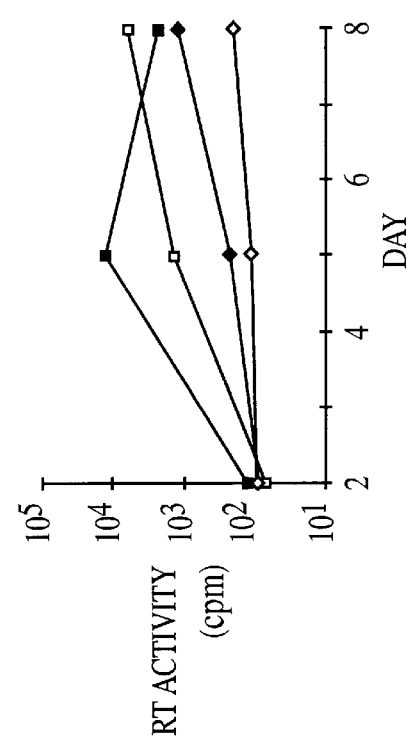
FIG. 4Ai
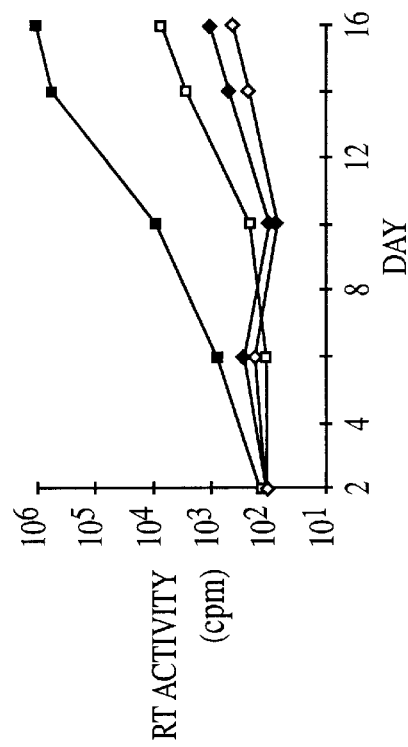
FIG. 4Aii
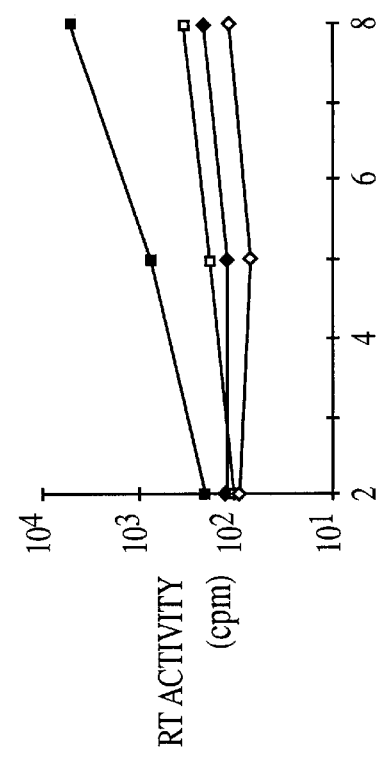
FIG. 4Aiii
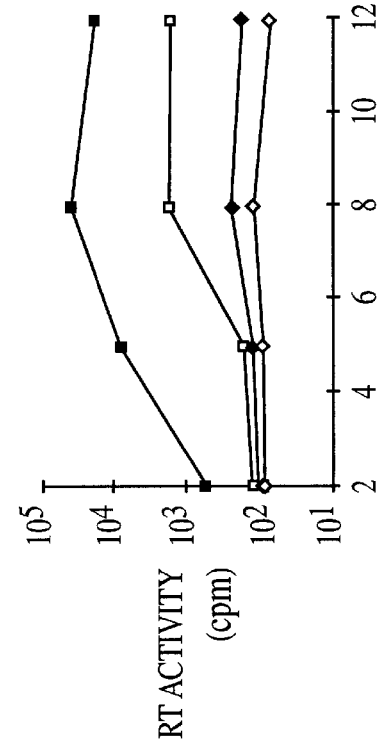
FIG. 4Aiv

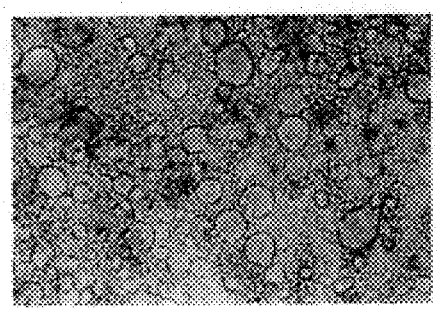
FIG. 4Bi
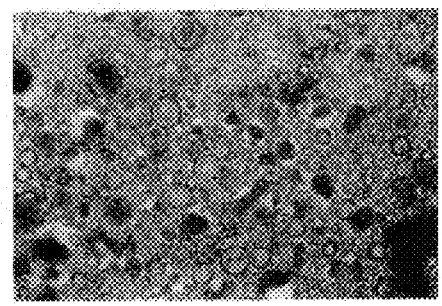
FIG. 4Bii
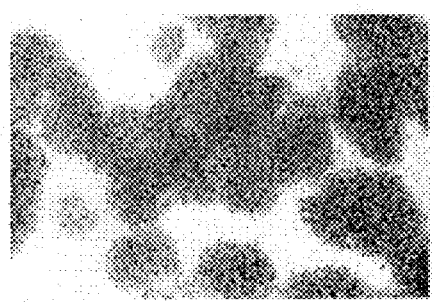
FIG. 4Biii
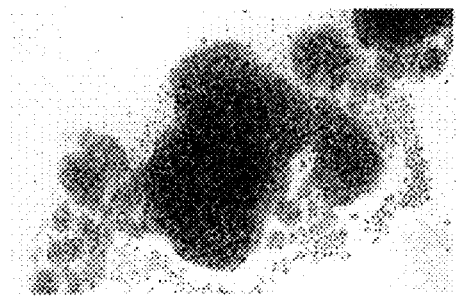
FIG. 4Biv

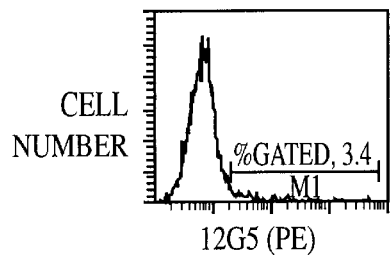
FIG. 5Ai
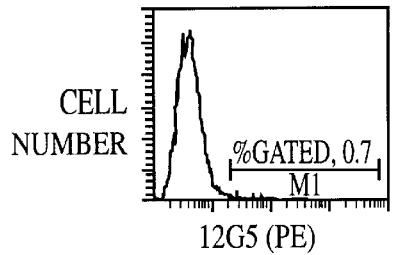
FIG. 5Aii
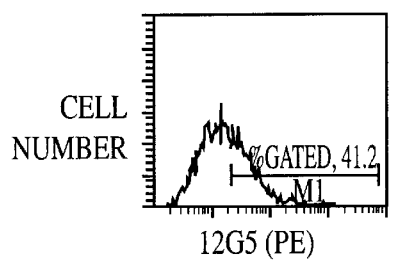
FIG. 5Aiii
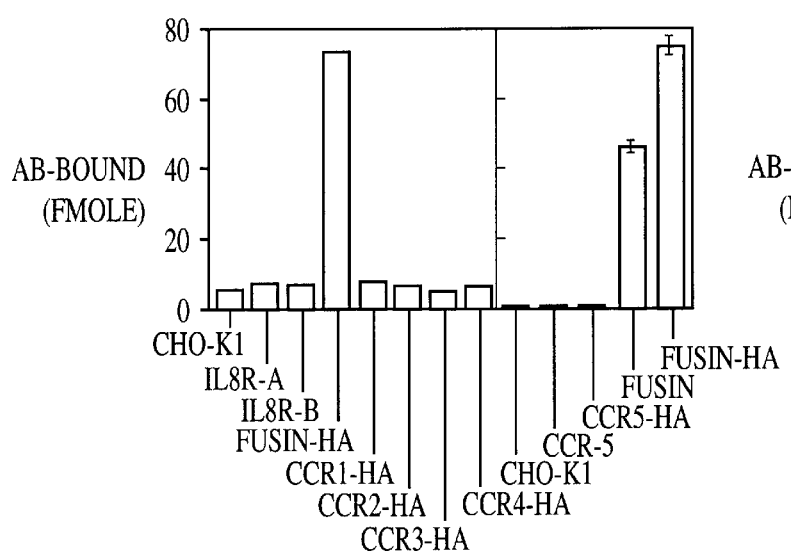
FIG. 5Bi
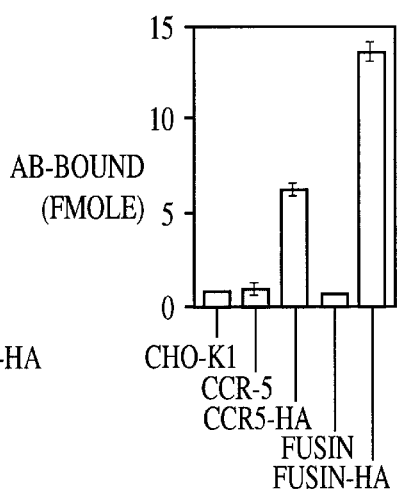
FIG. 5Bii

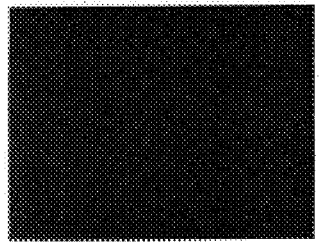
FIG. 5Ci
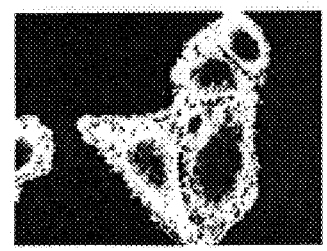
FIG. 5Cii
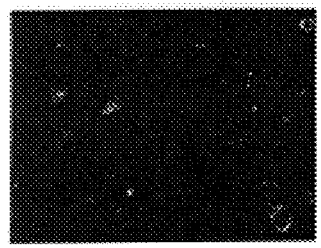
FIG. 5Ciii
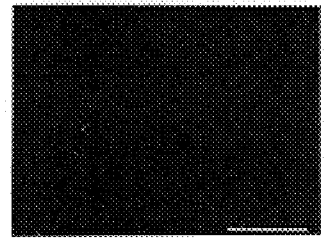
FIG. 5Civ
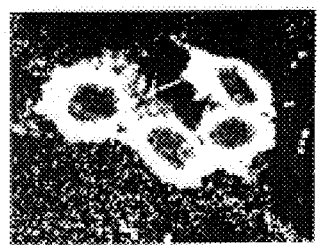
FIG. 5Cv
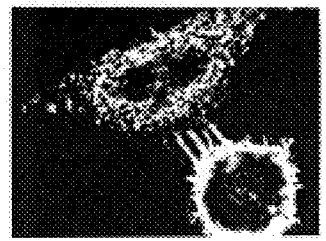
FIG. 5Cvi

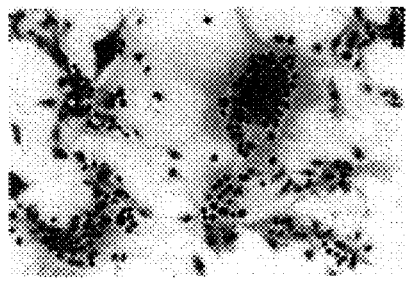
FIG. 6Ai
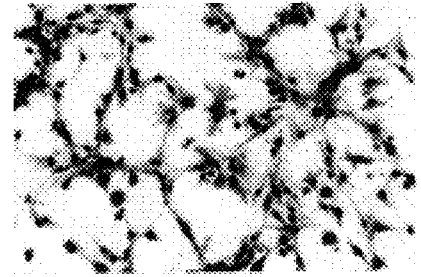
FIG. 6Aii
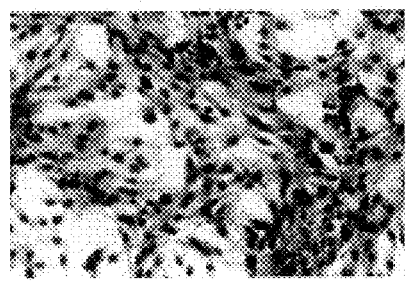
FIG. 6Aiii
FIG. 6Aiv

ANTIBODIES DIRECTED AGAINST CELLULAR CORECEPTORS FOR HUMAN IMMUNODEFICIENCY VIRUS AND METHODS OF USING THE SAME

CROSS REFERENCE TO RELATED APPLICATIONS

This application claims priority under 35 U.S.C. §119(e)(1) to U.S. Provisional Application Ser. Nos. 60/020,396 and 60/020,647, filed on Jun. 25 and Jun. 27, 1996, respectively.

GOVERNMENT SUPPORT

The invention was supported in part by a grant from the U.S. Government (NIH Grant No. AI 33854) and the U.S. Government may therefore have certain rights in the invention.

FIELD OF THE INVENTION

The field of the invention is infection by and pathogenesis of Human Immunodeficiency Virus.

BACKGROUND OF THE INVENTION

The human immunodeficiency viruses HIV-1 and HIV-2 and the closely related simian immunodeficiency viruses (SIV), all use the CD4 molecule as a receptor during infection. Other cellular molecules have long been suspected to form an essential component of the cellular HIV receptor; however, the nature of such cellular molecules was not known until the discovery of fusin (Feng et al., 1996, Science 272:872–876; Maddon et al., 1986, Cell 47:333–348; Dragic et al., 1995, J. Virol. 69:1013–1018; Clapham et al., 1992, J. Virol. 66:3531–3537; Chesebro et al., 1990, J. Virol. 64:215–221; Stefano et al., 1993, J. Virol 67:6707–6715; Hoxie et al., 1988, J. Virol. 62:2557–2568).

Recently, two molecules, fusin, which is now known as CXCR4 (also known as Lestr, LCR-1, and HUMSTR) and CCR5, which are members of the chemokine receptor family of proteins, have been shown to function with CD4 as coreceptors for HIV-1 isolates that are tropic for T-cell lines or macrophages, respectively (Feng et al., 1996, Science 272:872–876; Alkhatib et al., 1996, Science 272:1955–1958; Deng et al., 1996, Nature 381:661–666; Dragic et al., 1996, Nature 381:667–673). Other molecules in this family including CCR3 and CCR2b, also appear to function as cofactors for some HIV-1 isolates (Doranz et al., 1996, Cell 85:1149–1158; Berson et al., 1997, J. Virol. 71:1692–1696; Choe et al., 1996, Cell 85:1135–1148). Moreover, recent studies have also implicated CCR5 and CXCR4 as coreceptors for isolates of simian immunodeficiency viruses (SIV) and HIV-2, respectively. This, indicates that the use of chemokine receptors is a general property of all human and nonhuman lentiviruses.

In addition to studies on CD4-dependent infection, several reports have demonstrated that some HIV isolates are capable of infecting lymphoid cells (Clapham et al., 1992, supra; Clapham, 1991, Rev. in Med. Virol. 1:51–58; McKnight et al., 1994, Virology 201:8–18) or non-lymphoid cells (Clapham et al., 1992 supra; Harouse et al., 1991, Science 253:320–323; Tateno et al., 1989, Proc. Natl. Acad. Sci. USA 86:4287–4290; Li et al., 1990, J. Virol. 64:1383–1387; Ikeuchi et al., 1990, J. Virol. 64:4226–4231) in the absence of CD4. Although infection of CD4-negative cells generally proceeds slowly and without cytopathic effects, some isolates of HIV-2 infect CD4-negative cells rapidly and cause extensive cell fusion (Clapham et al., 1992, supra). The highly cytopathic nature of these infections has suggested that these isolates can utilize one or more receptors other than CD4 with high efficiency.

HIV-1 strains exhibit distinct tropisms for CD4-positive cells. Macrophage tropic (M-tropic) strains of HIV-1 enter and replicate in macrophages and primary T cells but generally fail to enter T cell lines. These isolates characteristically do not induce multinucleated giant cells when cultured with certain immortalized T cell lines and are generally non-syncytium inducing (NSI). In contrast, T cell tropic strains fail to enter macrophages efficiently but readily infect primary T cells and induce syncytia (SI) on some T cell lines (Fauci et al., 1996, Nature 384:529–534). This difference in cell tropism has been shown to correlate with disease progression in that HIV strains isolated from individuals early in the course of their infection are M-tropic and NSI, while viruses isolated from individuals with advanced immunodeficiency are typically T-tropic and SI.

CXCR4 is a cellular protein which in conjunction with CD4, forms a functional cellular receptor for entry of certain strains of HIV into cells. This protein is a member of a family of molecules that bind chemokines which are involved in the trafficking of T cells and phagocytic cells to areas of inflammation (Power and Wells, 1996, Trends Pharmacol. Sci. 17:209–213). The chemokines MIP-alpha and MIP-beta and RANTES all bind to CCR5 while stromal cell derived factor (SDF-1) binds to CXCR4 (Bluel, et al., 1996, Nature 382:829–832; Oberlin et al., 1996, Nature 382:833–835). Recent reports have indicated that the viral envelope glycoprotein gp120 interacts directly with chemokine receptors (Lapham et al., 1996, Science 274:602–605; Moore, 1997, Science 276:51; Wu et al., 1996, Nature 384:179–183; Hesselgesser et al., 1997, Current Biology 7:112–121), generally at a step following CD4 binding.

CXCR4 fulfills the requirements of an HIV receptor co-factor. It renders a number of murine, feline, simian, quail, and hamster cell lines, as well as human cell lines, which cells are normally resistant to HIV-1 entry, fully permissive for HIV-1 env mediated syncytia formation. In addition, the T cell tropic HIV strain HIV-1 IIIB, is capable of infecting both murine and feline cells which co-express human CD4 and CXCR4. However, the macrophage tropic strain Ba-L, is not capable of infecting cells which co-express both CXCR4 and CD4. These results suggest that CXCR4 can serve as a co-factor for T-tropic, but not M-tropic, HIV-1 strains (Feng et al., 1996, supra). Moreover, the finding that change from M to T-tropic viruses over time in infected individuals correlates with disease progression suggests that the ability of the viral envelope to interact with CXCR4 represents an important feature in the pathogenesis of immunodeficiency and the development of full blown AIDS.

Current anti-HIV therapy includes the use of compounds which inhibit various aspects of HIV replication in a cell such as inhibition of replication and/or transcription of viral nucleic acid and inhibition of protein processing. While these therapies, particularly when used in combination with one another, are effective, they are frequently short-lived in that viral strains rapidly develop that are resistant to one or more of the compounds used. There therefore remains an acute need to develop additional therapies and strategies for preventing HIV infection in humans.

SUMMARY OF THE INVENTION

The invention relates to an antibody capable of binding to a cellular protein, which antibody has antiviral activity by virtue of the fact that the cellular protein to which the antibody binds is a protein which is required for entry of virus into a cell expressing that protein.

One aspect of the invention relates to an anti-immunodeficiency virus antibody capable of binding to a cellular protein. In another aspect, the immunodeficiency virus is selected from the group consisting of HIV-1, HIV-2 and SIV.

In yet another aspect of the invention, the protein to which the antibody of the invention binds is a chemokine receptor protein, preferably, an HIV receptor protein and/or a cellular cofactor for a cellular HIV receptor protein.

More preferably, the protein to which the antibody of the invention binds is selected from the group consisting of CXCR4 and CCR5; and most preferably, the protein to which the antibody binds is CXCR4.

In another aspect of the invention, the antibody is selected from the group consisting of a monoclonal antibody and a synthetic antibody. Preferably, the antibody is a monoclonal antibody, and more preferably, the antibody is MAb 12G5.

The invention also relates to an isolated DNA encoding an anti-immunodeficiency virus antibody capable of binding to a cellular protein.

In one aspect, the immunodeficiency virus is selected from the group consisting of HIV-1, HIV-2 and SIV.

In another aspect, the protein to which the antibody of the invention binds is a chemokine receptor protein. Preferably, the protein is an HIV receptor protein and/or a cellular cofactor for a cellular HIV receptor protein. More preferably, the protein is selected from the group consisting of CXCR4 and CCR5; and most preferably, the protein is CXCR4 and the antibody is the monoclonal antibody (MAb) 12G5.

The invention also relates to a method of inhibiting infection of a cell by HIV comprising adding to the cell an anti-immunodeficiency virus antibody capable of binding to a cellular protein on the cell, wherein upon binding of the antibody to the cellular protein infection of the cell by HIV is inhibited.

Also included in the invention is a method of treating HIV infection in a human comprising administering to the human an anti-immunodeficiency virus antibody capable of binding to a cellular protein on a cell, wherein upon binding of the antibody to the cellular protein, infection of the cell by HIV is inhibited, thereby treating the HIV infection in the human.

The invention further includes a method of obtaining an anti-immunodeficiency virus antibody capable of binding to a cellular protein on a cell, the method comprising generating a panel of antibodies directed against HIV infected or SIV infected cell proteins, and screening the antibodies for anti-immunodeficiency virus activity to obtain an antibody capable of binding to a cellular protein, which antibody has anti-immunodeficiency virus activity.

Also included in the invention is a method of identifying a target cell for immunodeficiency virus infection, the method comprising adding to a population of cells an anti-immunodeficiency virus antibody capable of binding to a cellular protein on a cell, wherein binding of the antibody to a cell in the population is an indication that the cell is an immunodeficiency virus target cell.

In addition, there is provided a method of identifying a candidate anti-immunodeficiency virus compound. This method comprises isolating a test compound capable of binding to an anti-immunodeficiency virus antibody, which antibody binds to a cellular protein, and assessing the ability of the test compound to inhibit infection of a cell by an immunodeficiency virus in an antiviral assay, wherein inhibition of infection of the cell by the immunodeficiency virus in the presence of the test compound is an indication that the test compound is an anti-immunodeficiency virus compound.

The invention also includes a method of measuring the level of expression of CXCR4 on a cell comprising adding to the cell an antibody which binds to the CXCR4 and assessing the amount of antibody bound to the cell, wherein the amount of the antibody bound to the cell is a measure of the level of expression of the CXCR4 on the cell.

BRIEF DESCRIPTION OF THE DRAWINGS

FIG. 1A is a series of graphs graph depicting detection of CXCR4 cell surface glycoprotein expression following staining of MOLT-4, C8166, U87/CD4 and RD/CD4 cells and primary human macrophages (MAC) cultured for 1 and 5 days.

FIG. 1B is an image of Northern blot analysis of the indicated cells using CXCR4 or GAPDH nucleic acid as a probe.

FIG. 1C is an image of reverse transcriptase (RT) PCR analysis on the indicated cells using CXCR4 or GAPDH nucleic acid as a probe.

FIG. 3C is a series of images of syncytium induction assays which were performed on the indicated target cells by cocultivation with HIV-2/vcp-infected BC7 cells or HIV-1/LAI-infected Hut-78 cells in the presence or absence of 10 $\mu$g/ml of anti-CD4 MAb #19. Cultures were photographed after either 24 or 48 hours. As shown, extensive syncytia formation is induced by HIV-2/vcp on CD4-negative BC7 cells which is unaffected by the addition of anti-CD4 MAb.

FIG. 4A is a series of graphs depicting inhibition of CP-MAC and HIV-2/vcp infection by the 12G5 MAb. Sup-T1 cells or CD4-negative BC7, Na1m6 and Daudi cells were preincubated with the indicated concentrations of 12G5 MAb and were then inoculated with the viruses shown. RT activity in infected cell supernatants was assessed at the indicated times. Dose-dependent inhibition of CP-MAC and HIV-2/vcp infection by 12G5 MAb is shown.

FIG. 4B is a series of images depicting inhibition of CP-MAC and HIV-2/vcp syncytia induction by the 12G5

MAb. Sup-T1 or BC7 cells were cultured with either CP-MAC-infected Sup-T1 cells, or HIV-2/vcp-infected BC7 cells in the presence or absence of 12G5 (10 μg/ml). Cells were photographed after 48 hours of culture. Inhibition of syncytium formation by 12G5 is evident in cells infected with either virus.

FIG. 5A is a series of graphs depicting reactivity of 1 2G5 MAb with CXCR4. U87 cells stably expressing either CXCR4, CCR1, or the control vector pBABe-puro (Deng et al., 1996, Nature 381:661–666), were evaluated for reactivity with 12G5 (10 μg/ml) by FACS. The region for positivity, designated M1, was defined using a non-reactive control MAb, and the percent of cells falling within this window for each sample is indicated. As shown, a marked shift in reactivity was observed in the entire population of CXCR4-expressing cells.

FIG. 5B is a graph depicting reactivity of 12G5 MAb with CXCR4. Control CHO cells or cells stably expressing HA-tagged CXCR4 or the other chemokine receptors indicated were evaluated for reactivity to $^{125}$I-12G5, using protocols described in Pelchen-Matthews et al. (1989, EMBO J. 8:3641–3649). Scatchard type analysis indicated that the $K_d$ for 12G5 binding to CHO-CXCR4 cells was 1–5 nM; $^{125}$I-12G5 binding was competed to close to background levels by 100 nM of unlabeled 12G5 but was not influenced by the anti-HA antibody 12G5.

FIG. 5C is a series of photographs depicting immunofluorescence confocal microscopy of CHO cells stably expressing CXCR4 or chemokine receptors using 12G5. CHO-K1 cells expressing HA-tagged CXCR4 or the human IL8R-B receptor were stained with 12G5, the anti-human CD4 MAb Q4120, or an antibody against the HA-tag (Pelchen-Matthews et al. (1989, supra). Only cells with HA-tagged CXCR4 stained with MAb 12G5, while both samples stained brightly with the anti-HA MAb. None of the cells exhibited staining with Q4120. Similarly, no binding of MAb 12G5 was seen in CHO cells stably expressing IL8R-A, or CCR1, CCR2b, CCR3 or CCR4, or in cells transiently expressing CCR5. Scale bar=20 μm.

FIG. 6A is a series of photographs depicting the fact that recombinant CXCR4 is sufficient to render U87 cells susceptible to HIV-2/vcp syncytium induction. U87 cells stably expressing either CXCR4 or CD4, or untransduced cells (control) were cocultured with HIV-2/vcp infected BC7 cells and syncytium formation was assessed by photography. Large syncytia are evident only in U87 cells which express CXCR4. Induction of syncytia was completely inhibited in cells which were preincubated with 12G5 (10 μg/ml).

Figure 6B:
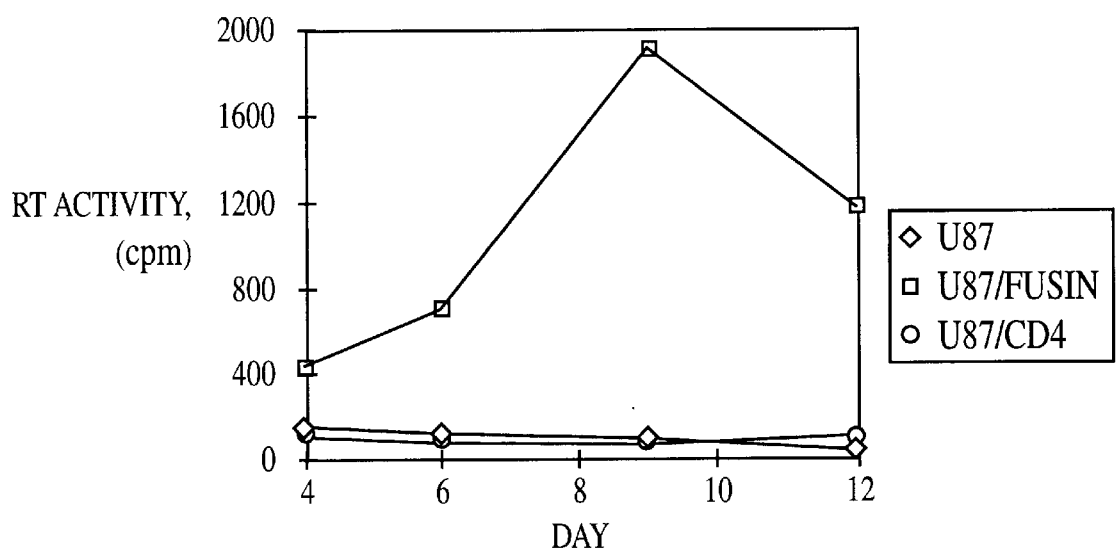

FIG. 6B is a graph depicting the fact that recombinant CXCR4 is sufficient to render U87 cells susceptible to HIV-2/vcp infection. Cells were inoculated with cell-free HIV-2/vcp (1000 TCID$_{50}$ units, determined on BC7 cells) and the amount of RT in the culture supernatants was monitored at the indicated time points. Only CXCR4-expressing cells were infected with virus. Extensive syncytia formation and cell killing were also observed in the infected CXCR4-expressing cells which correlated with the time of production of RT.

Figure 7:
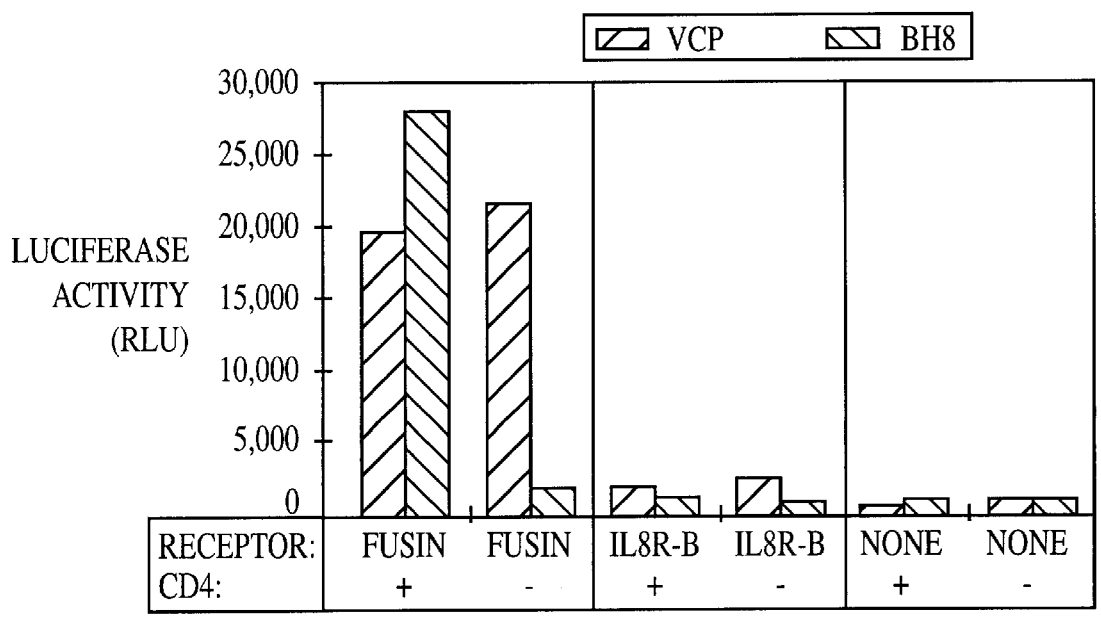

FIG. 7 is a graph depicting induction of cell fusion by the HIV-2/vcp envelope glycoprotein in a gene reporter fusion assay. HeLa effector cells were transfected with pCR3.1 expressing either HIV-2/vcp env or BH8 HIV-1 env clones and were then infected with vaccinia virus. QT6 target cells were transfected with constructs expressing CXCR4, IL8R-B or the PCR3.1 expression vector alone, and a plasmid containing the luciferase gene driven by a T7 promoter (Promega Biotech). Where indicated, target cells were also infected with pT4, which constitutively expresses CD4 from the CMV promoter. Luciferase activity as an indication of cell fusion is indicated in terms of relative light units (RLU) as described (Doranz et al., 1996, Cell 85:1149–1158).

Figure 8A:
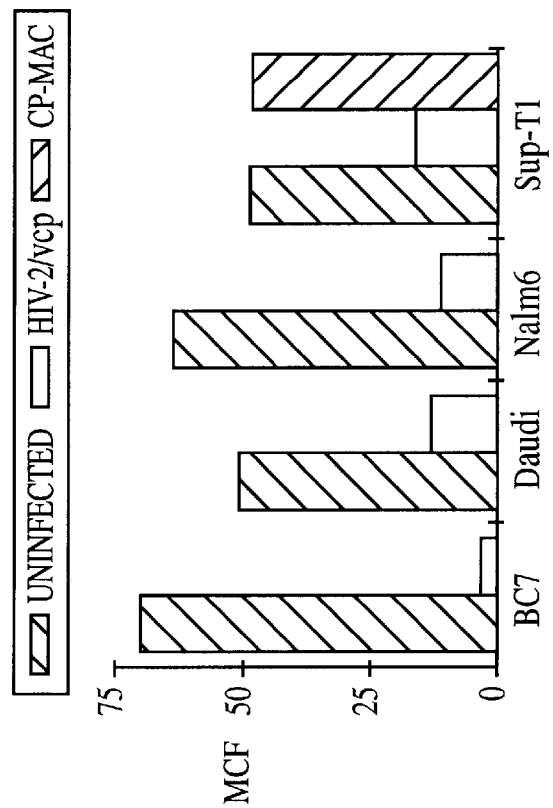
Figure 8B:
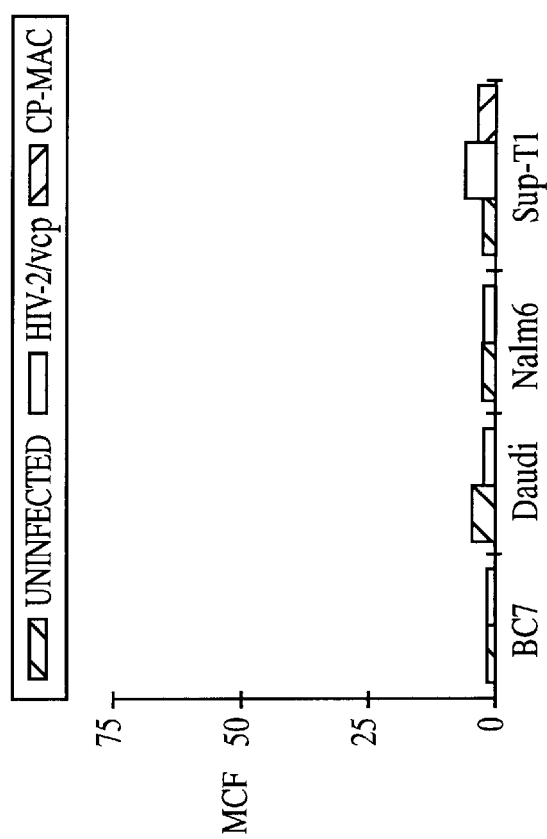

FIG. 8 is a series of graphs depicting downregulation of CXCR4 expression by HIV-2/vcp infection. BC7, Daudi, Na1m6 or Sup-T1 cells that were either uninfected or infected with the indicated viruses were evaluated for surface reactivity by FACS either with an isotope-matched control MAb or MAb 12G5 (10 μg/ml) and the mean channel fluorescence intensity (MCF) is shown for each cell type. Loss of MAb 12G5 reactivity is seen on HIV-2/vcp-infected but not CP-MAC-infected cells. No reduction was seen in expression of HLA class-I using MAb W6/32. The data are representative of three experiments from two separate infections.

DETAILED DESCRIPTION OF THE INVENTION

The invention relates to an antiviral antibody which binds to a cellular protein essential for entry of a virus into a cell expressing that protein.

The antibody of the invention is an antiviral antibody in that it is an antibody which binds to a specific cellular protein which is essential for virus entry into the cell in which the cellular protein is expressed. By binding to the cellular protein, the antibody of the invention inhibits entry of the virus into the cell and is therefore termed an antiviral antibody despite the fact that it does not bind to a viral protein, but rather, binds to a cellular protein.

The virus against which the antiviral antibody is directed is an immunodeficiency virus, that is, a virus which causes an immunodeficiency disease. Thus, the antibody of the invention is termed an anti-immunodeficiency virus antibody. Such immunodeficiency virus should be construed to include any strain of HIV or SIV.

By "HIV" as used herein, is meant any strain of a human immunodeficiency virus belonging to the group of either HIV type 1 or HIV type 2. By "SIV" as used herein is meant any of five recognized strains of SIV (SIVmac, SIVsmm, SIVagm, SIVmnd and SIVcpz) which are known to infect non-human primates.

The antibody of the invention is an antibody which is capable of binding to a cellular protein required to form a functional cellular receptor for entry of HIV into a cell. The antibody of the invention may be a monoclonal antibody (MAb) or may be antibody which is derived from a phage library or a humanized or a synthetic antibody, or an antibody fragment expressed intracellularly.

The antibody of the invention is an antibody which binds to a cellular co-factor required for entry of HIV into a cell.

A "cellular co-factor" as used herein, is defined as a protein which is required, in association with a cellular receptor for HIV, for entry of HIV into cells.

Since the preferred antibody of the invention, MAb 12G5, binds to a protein which is both a cellular cofactor and an HIV-receptor protein, depending upon the cell type to be infected, it will be appreciated that the antibody of the invention should be construed to be one which binds to a cellular protein which may be a cellular cofactor and may also be a receptor protein in its own right. In other words, the antibody of the invention is one which binds to a cellular protein which is necessary for virus entry into cells. Since binding of the antibody to the cellular protein serves to block virus entry into cells, the antibody is an antiviral antibody.

Preferably, the antibody of the invention is directed against the cellular protein CXCR4; more preferably, the antibody is a monoclonal antibody and even more preferably, the antibody of the invention is MAb 12G5.

According to the invention, the antibody of the invention is useful in a method of inhibiting infection of a cell by HIV as described herein. The antibody is further useful for the generation of antibody derivatives which are useful for inhibiting infection of a cell by HIV also as described herein. Moreover, the antibody of the invention is useful in a method of screening compounds for anti-HIV activity as described herein. Additional uses for the antibody of the invention include the identification of cells in the body which are potential targets for viral infection. The antibody is thus also useful for the isolation of such cells using flow cytometry technology or other cellular isolation techniques which are common in the art. The invention also relates to methods of use of the antibody of the invention, which methods include diagnostic and therapeutic uses.

The antibody or derivatives thereof may be expressed intracellularly, reducing CXCR4 expression on the cell surface and rendering these cells resistant to HIV infection. In addition, the antibody of the invention inhibits SDF-1 binding and signalling by CXCR4. Thus, the antibody or derivatives thereof, may be used to antagonize SDF-1 function in vivo.

The antibody of the invention, exemplified herein by the MAb 12G5, was generated in a hybridoma screening protocol in which mice were immunized with an SIV-infected human cell line in order to generate MAbs reactive with the SIV envelope glycoproteins. Eight MAbs were generated which exhibited potent antiviral properties. Of these eight MAbs, seven reacted specifically with the viral envelope glycoproteins, while one antibody, MAb 12G5, reacted with both infected and uninfected cells. This result was unexpected since the protocol was originally designed to identify MAbs specific for viral proteins and the screening assay was an antiviral assay. Thus, the MAbs which were generated following immunization of mice with SIV-infected human cells were screened for antiviral activity, i e., a functional antiviral assay was used to select the MAbs, rather than the more common antigen-antibody binding assay. Since this assay was expected to reveal the presence of MAbs which bind viral antigens, the generation of an antiviral MAb specific for a cellular protein was unexpected.

The preferred antibody of the invention, MAb 12G5, was discovered to bind to a cell protein termed CXCR4, which protein is essential for entry of an immunodeficiency virus into cells. Since MAb 12G5 possesses antiviral activity, this antibody is specific for epitopes on CXCR4 which are essential for virus infection. The functional assay by which the antibody is generated is unique in that it facilitates the identification of an antiviral antibody which binds a cellular protein rather than a viral protein.

As the data presented herein establish, in some instances, CXCR4 functions as a cellular co-factor for entry of HIV into cells using CD4 as the cellular receptor molecule. In other instances, CXCR4 functions as a cellular receptor for HIV in the absence of CD4. Thus, CXCR4 is both a cellular co-factor, as defined herein, and is a cellular virus receptor protein in its own right for the entry of HIV into certain cells.

As described in detail herein, MAb 12G5 is specific for CXCR4. MAb 12G5 binds to both human and nonhuman cell lines following transient or stable cellular expression of a recombinant CXCR4 protein. In addition, in assays designed to evaluate the antiviral effects of MAb 12G5, this antibody is capable of inhibiting both infection as well as syncytia formation by a number of HIV-1, HIV-2 and SIV isolates. The extent of inhibition of virus replication is dependent upon the test virus and also the target cell.

By "antiviral activity" as used herein, is meant an antibody which when added to an immunodeficiency virus or to a cell to be infected with such a virus, mediates a reduction in the ability of the virus to infect and/or replicate in the cell compared with the ability of virus to infect and/or replicate in the cell in the absence of the antibody. Examples of assays for antiviral activity are described in detail in the experimental detail section and include, but are not limited to, reverse transcriptase assays, immunofluorescence assays, assays for formation of syncytia, antigen capture assays and the like.

To generate the antibody of the invention, wherein the antibody is a monoclonal antibody, cells which are suspected to encode a cellular protein essential for virus entry are first infected with HIV or SIV. Extracts are prepared from the cells and are used to generate a panel of monoclonal antibodies directed against the infected cells. Antibodies are screened for antiviral activity in a functional antiviral assay as described herein, and for the ability to bind cellular rather than viral proteins, also as described herein. Antiviral antibodies which bind cellular proteins are selected and are further characterized with respect to the proteins to which they bind and to their antiviral capabilities.

Preferably, the entire CXCR4 molecule is used to generate anti-CXCR4 antibodies since the entire molecule is in the correct conformation for the generation of anti-CXCR4 antibodies which block virus entry into cells. However, the invention should not be construed to be limited solely to the use of the entire CXCR4 molecule for the generation of antibodies, it being understood that peptides, which can be made according to well known procedures, may also be used provided they give rise to an antibody having the characteristics described herein.

It should be appreciated that the present invention also provides for analogs of CXCR4 obtained according to the methods of the invention. Analogs may differ from naturally occurring proteins by conservative amino acid sequence differences or by modifications which do not affect sequence, or by both.

For example, conservative amino acid changes may be made, which although they alter the primary sequence of the peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of proteins, e.g., acetylation, or carboxylation. Also included are modifications of glycosylation, e.g., those made by modifying the glycosylation patterns of a protein during its synthesis and processing or in further processing steps; e.g., by exposing the protein to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are proteins which have been modified using ordinary molecular biological techniques so as to improve their resistance to proteolytic degradation or to optimize solubility properties. Analogs of such proteins include those containing residues other than naturally occurring L-amino acids, e.g., D-amino acids or non-naturally occurring synthetic amino acids. The proteins of the invention are not limited to products of any of the specific exemplary processes listed herein.

The present invention should therefore be construed to include unmodified or modified CXCR4, which CXCR4 is capable of eliciting the production of an antibody specific for CXCR4 and which antibody has antiviral activity as defined herein. Preferably, the CXCR4 used to generate the antibody of the invention is CXCR4 located within the context of a cell.

Given the advances in technology in cloning DNA encoding proteins comprising antibodies, the invention should also be construed to include DNA which encodes the antibody of the invention, or a portion of such antibody.

When the antibody of the invention is a monoclonal antibody, the nucleic acid encoding the antibody may be cloned and sequenced using technology which is available in the art, and is described, for example, in Wright et al. (1992, Critical Rev. in Immunol. 12(3,4):125–168) and the references cited therein. Further, the antibody of the invention may be "humanized" using the technology described in Wright et al., (supra) and in the references cited therein.

For example, to generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, *Molecular Cloning: A Laboratory Manual*, Cold Spring Harbor, N.Y.).

Bacteriophage which encode the desired antibody, e.g., an antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al., (supra).

Processes such as those described above, have been developed for the production of human antibodies using M13 bacteriophage display (Burton et al., 1994, *Adv. Immunol.* 57:191–280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The invention thus includes a DNA encoding the antibody of the invention or a portion of the antibody of the invention. To isolate DNA encoding an antibody, for example, DNA is extracted from antibody expressing phage obtained according to the methods of the invention. Such extraction techniques are well known in the art and are described, for example, in Sambrook et al. (supra).

The isolated DNA encoding an anti-CXCR4 antibody may be constructed such that it is useful for intracellular immunization of a cell against immunodeficiency virus infection. For example, single chain fragments from the variable region of the antibody that contain the CXCR4 binding site could be expressed at intracellular sites. This expression is predicted to interfere with the delivery of the native cellular CXCR4 protein to the cell surface, thereby rendering these cells resistant to infection with HIV. This general approach is useful for engineering immune or hematopoietic stem cells resistant to HIV infection and provides a novel gene therapy approach for treatment of HIV infected individuals.

An "isolated DNA", as used herein, refers to a DNA sequence, segment, or fragment which has been purified from the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to DNA which has been substantially purified from other components which naturally accompany the DNA, e.g., RNA or DNA or proteins which naturally accompany it in the cell.

The invention should also be construed to include DNAs which are substantially homologous to the DNA isolated according to the method of the invention. Preferably, DNA which is substantially homologous is about 50% homologous, more preferably about 70% homologous, even more preferably about 80% homologous and most preferably about 90% homologous to DNA obtained using the method of the invention.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGCG5' share 50% homology.

To obtain a substantially pure preparation of a protein comprising, for example, an antibody, generated using the methods of the invention, the protein may be extracted from the surface of the phage on which it is expressed. The procedures for such extraction are well known to those in the art of protein purification. Alternatively, a substantially pure preparation of a protein comprising, for example, an antibody, may be obtained by cloning an isolated DNA encoding the antibody into an expression vector and expressing the protein therefrom. Protein so expressed may be obtained using ordinary protein purification procedures well known in the art.

As used herein, the term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state.

To inhibit infection of cells by HIV in vitro, cells are treated with the antibody of the invention, or a derivative thereof, either prior to or concurrently with the addition of virus. Inhibition of infection of the cells by the antibody of the invention is assessed by measuring the replication of virus in the cells, by identifying the presence of viral nucleic acids and/or proteins in the cells, for example, by performing PCR, Southern, Northern or Western blotting analyses, reverse transcriptase (RT) assays, or by immunofluorescence or other viral protein detection procedures. The amount of antibody and virus to be added to the cells will be apparent to one skilled in the art from the teaching provided herein.

To inhibit infection of cells by HIV in vivo, the antibody of the invention, or a derivative thereof, is administered to a human subject who is either at risk of acquiring HIV infection, or who is already infected with HIV. Prior to administration, the antibody, or a derivative thereof, is suspended in a pharmaceutically acceptable formulation such as a saline solution or other physiologically acceptable solution which is suitable for the chosen route of administration and which will be readily apparent to those skilled in the art of antibody preparation and administration. The dose of antibody to be used may vary dependent upon any number of factors including the age of the individual, the route of administration and the extent of HIV infection in the individual. The antibody is prepared for administration by being suspended or dissolved in a pharmaceutically acceptable carrier such as saline, salts solution or other formulations apparent to those skilled in such administration.

Typically, the antibody is administered in a range of 0.1 $\mu$g to 1 g of protein per dose. Approximately 1–10 doses are administered to the individual at intervals ranging from once per day to once every few years. The antibody may be administered by any number of routes including, but not limited to, subcutaneous, intramuscular, oral, intravenous, intradermal, intranasal or intravaginal routes of administration. The antibody of the invention may be administered to the patient in a sustained release formulation using a biodegradable biocompatible polymer, or by on-site delivery using micelles, gels and liposomes, or rectally (e.g., by suppository or enema). The appropriate pharmaceutically acceptable carrier will be evident to those skilled in the art and will depend in large part upon the route of administration.

Derivatives of the antibody of the invention may be prepared using technology common in the art and described, for example in Harlow et al. (1988, *In: Antibodies,* A Laboratory Manual, Cold Spring Harbor, N.Y.) and in Sambrook et al. (1989, Molecular Cloning: A Laboratory Manual, Cold Spring Harbor, N.Y.). Further, derivatives of the antibody of the invention, including fragments of antibodies and fusion antibodies may be generated following the teaching in Clackson et al. (1991, Nature 352:624) and in other references teaching Fab antibody fragments and chimeric antibodies, such as Jonker et al. (1993, Clin. Exp. Immunol. 93:301–307), Leung et al. (1994, Hybridoma 13:469–476); Sung Co et al. (1992, J. Immunol. 148:1149–1154); and, LoBuglio et al. (1989, Proc. Natl. Acad. Sci. USA 86:4220–4224).

The antibody of the invention may also be used in a method of screening compounds for anti-HIV activity. A test compound is first screened for the ability to bind to the antibody of the invention. Compounds which bind to the antibody are likely to share structural and perhaps biological activities with CXCR4 and thus, may serve as competitive inhibitors for inhibition of the interaction of HIV envelope protein with CD4 and/or CXCR4 plus CD4. An antibody-binding compound is further tested for antiviral activity by treating cells with the compound either prior to or concurrently with the addition of virus to the cells. Alternatively, the virus and the compound may be mixed together prior to the addition of the mixture to the cells. The ability of the compound to affect virus infection is assessed by measuring virus replication in the cells using any one of the known techniques, such as a RT assay, immunofluorescence assays and other assays known in the art useful for detection of viral proteins or nucleic acids in cells. Generation of newly replicated virus may also be measured using known virus assays such as those which are described herein.

The antibody of the invention may also be used in competition assays to screen for compounds that bind to CXCR4 and which therefore prevent binding of the antibody to CXCR4. Such compounds, once identified, may be examined further to determine whether or not they prevent entry of virus into cells. Compounds which prevent entry of virus into cells are useful as anti-viral compounds.

Additional uses for the antibody of the invention include the identification of cells in the body which are potential targets for infection by an immunodeficiency virus.

By the term "target cell for immunodeficiency virus infection" as used herein, is meant a cell which expresses receptor protein(s) for an immunodeficiency virus and which cell is therefore capable of being infected by an immunodeficiency virus.

Cells which are potential targets for HIV infection may be identified by virtue of the presence of CXCR4 on their surface. The antibody of the invention facilitates identification of these cells as follows: The antibody of the invention is first combined with an identifiable marker, such as an immunofluorescent or radioactive marker. Cells which are obtained from a human subject are then reacted with the tagged antibody. Binding of the antibody to cells is an indication that such cells are potential targets for HIV infection. The identification of cells which may be infected with HIV is important for the design of therapies for the prevention of HIV infection. For example, CXCR4 is differentially expressed and regulated on human T lymphocytes (Bleul et al., 1997, Proc. Natl. Acad. Sci. USA 94:1925–1930). Further, reactivity of immune cells to MAb 12G5 is high on naive cells and low on memory cells and thus, the pattern of expression of CXCR4 and its utilization by viruses may contribute to immune dysfunction. CXCR4 has also been detected, using the monoclonal antibody of the invention, on some endothelial cells (in atherosclerotic plaques), platelets and some hematopoietic precursor cells. In the case of individuals who are infected with HIV, the identification of target cells provides an immune profile of these individuals which provides useful information regarding the progress of their infection.

In addition to the aforementioned uses for the monoclonal antibody of the invention, the antibody is useful for the detection of CXCR4 on a variety of cell types on which CXCR4 may be expressed. For example, CXCR4 is expressed on human neurons (Hesselgesser et al., 1997, Current Biology 7:112–121), including cells in the human brain.

Thus, the monoclonal antibody of the invention may be useful for monitoring CXCR4 expression levels on a variety of cell types, which expression may be an indication of a disease state in a human, including, but not limited to HIV infection, atherosclerosis, and the like.

Deposit. Under the terms of the Budapest Treaty on the International Recognition of the Deposit of Microorganisms for the Purpose of Patent Procedure, deposit of the cell line producing the monoclonal antibody, 12G5, was made on Jun. 25, 1997, with the American Type Culture Collection (ATCC) of Rockville, Md., USA, where the deposit is given ATCC Accession Number HB12371.

Applicant's assignee, the Trustees of the University of Pennsylvania, represents that the ATCC is a depository afforded permanence of the deposit and ready accessibility thereto by the public if a patent is granted. All restrictions on the availability to the public of the material so deposited will be irrevocably removed upon granting of a patent. The material will be readily available during the pendency of the patent application to one determined by the Commissioner to be entitled thereto under 37 C.F.R. §1.14 and 35 U.S.C. §122. The deposited material will be maintained with all the care necessary to keep it viable and uncontaminated for a period of at least five years after the most recent request for the furnishing of a sample of the deposited material, and in any case, for a period of at least thirty (30) years after the date of the deposit or for the enforceable life of the patent, whichever period is longer. Applicant's assignee acknowledges its duty to replace the deposit should the depository be unable to furnish a sample when requested due to the condition of the deposit.

The invention is now described in more detail in the experimental examples provided herein. The invention should not be construed to be limited to the experimental examples provided herein, but rather should be construed to include any and all variations as will become apparent to the artisan skilled in the art of antibody therapy when in possession of the present invention. Thus, the invention should in no way be construed as being limited to the following examples, but rather, should be construed to encompass any and all variations which become evident as a result of the teaching provided herein.

EXAMPLE 1

Inhibition of HIV by a Monoclonal Antibody to a Coreceptor (CXCR4) is both Cell Type and Virus Strain Dependent The data presented herein establish that 12G5 is a mouse MAb that specifically recognizes CXCR4 but not other members of the chemokine receptor family, including CCR1–5 and CXCR1 and CXCR2 (interleukin-8 receptors α and β, respectively).

In FIG. 1A there is shown the levels of cell surface CXCR4 expression determined by flow cytometry following 12G5 staining of the CD4$^+$ T-cell lines MOLT-4 and C8166, the CD4-transfected human rhabdomyosarcoma cell line RD, and the human glioma cell line U87 as well as primary macrophages purified by adherence to plastic and cultured for 1 or 5 days (McKnight et al., 1995, J. Virol. 69:3167–3170; and Simmons et al., 1995, Virology 209:696–700). Flow cytometry was carried out as previously described (McKnight et al., 1996, J. Virol. 70:4598–4606).

HIV infectivity of macrophages or PBMCs is routinely estimated by infecting cells that have been cultured for 5 days after purification from blood or buffy coats. It was therefore important to assess CXCR4 expression in cultures of this age. Prior to staining with 12G5, macrophages and PBMCs were preincubated with 5% heat-aggregated hyper-immune gamma globulin (Miles Cutler) on ice for 30 minutes to block any nonspecific binding to Fc receptors. FIGS. 1B and 1C show the results of reverse transcription-PCR (RT-PCR) and Northern blot analyses, respectively, of RNA prepared from the same cell types as shown in FIG. 1A. RNA for RT-PCR was prepared with RNA-zol. cDNA was then prepared from 5 μg of RNA by using Stratagene RTOPCR kit. One-twentieth of the cDNA prepared was included in the PCR reactions. PCR for CXCR4 used the primers 5'-TAG ATA TCT TAC CAT GGA GGG GAT CAG-3' [SEQ ID NO:1] and 5'-TAG CGG CGC TTA GTG GAG TGA AAA CTT G-3' [SEQ ID NO:2], corresponding to the positive and negative strands, respectively, and amplifying a 1,044-bp fragment. The positive-strand primer incorporated a 5' tail which encoded an EcoRV site, and the minus strand incorporated a 3' tail encoding a NotI site. Conditions for CXCR4 amplification were 30 cycles of 95° C. for 30 seconds, 50° C. for 30 seconds, and 75° C. for 1 minute. Glyceraldehyde-3-phosphate dehydrogenase (GAPDH) sequences were amplified by using the positive-strand primers 5'-TGG ATA TTG CCA TCA ATG ACC-3' [SEQ ID NO:3] and the negative-strand primer 5'-GAT GGC ATG GAC TGT GGT CAT G-3' [SEQ ID NO:4]. Conditions for the PCR were 40 cycles of 95° C. for 30 seconds, 65° C. for 1 minute, and 72° C. for 30 seconds. Control PCR analysis of the RNA preparations was consistently negative for both CXCR4 and GAPDH DNA. mRNA for Northern blot analysis was prepared from 10$^6$ to 10$^7$ cells Pharmacia Quickprep Micro mRNA isolation system), and 1 μg was fractionated on a 1.2% agarose-formaldehyde gel. RNA was transferred overnight onto a Genescreen Plus membrane (NEN) with 10× SSPE (1× SSPE is 0.18M NaCl, 10 mM NaH$_2$PO$_4$, and 1 mM EDTA) and then baked at 80° C. for 2 hours. $^{32}$P-labeled CXCR4 and GAPDH double-stranded probes were prepared by random priming (Amersham) and hybridized to the membrane in Quickhyb solution (Stratagene) for 1 hour at 65° C. The membrane was washed twice for 15 minutes at room temperature in 2× SSC (1× SSC is 0.15M NaCl plus 0.015M sodium citrate)-0.1% sodium dodecyl sulfate and once for 30 minute at 65° C. in 0.1× SSC-01.% sodium dodecyl sulfate. The blot was then exposed at −70° C. for 1 week.

Cell lines used in FIG. 1 and throughout this study, including RD/CD4, U87/CD4, HeLa/CD4, SCL/CD4, Daudi and CD4+ T-cell lines C8166, MOLT-4, MT-2, SSCEM, and Sup T1, have all been described (Chesebro et al., 1990, J. Virol. 64:215–221; Clapham et al., 1991, Virology 181:703–715; Clapham et al., 1992, J. Virol. 66:3531–3537; Clapham et al., 1987, Virology 158:44–51; Koot et al., 1992, AIDS 6:49–54; McKnight et al., 1994, Virology 201:8–18; Miyoshi et al., 1981, Nature 294:770–771; and Nara et al., 1988, Nature 332:469–470). WI-38t cells are simian virus 40-transformed counterparts of the WI-38 human diploid cell line (Pontén et al., 1962, J. Cell. Comp. Physiol. 61:145–163).

The data presented in FIG. 1 establish that 12G5 detection of cell surface CXCR4 by flow cytometry correlates well with CXCR4 mRNA detection by RT-PCR or by Northern blotting. Both CD4+ T-cell lines (MOLT-4 and C8166) as well as RD cells were highly positive for CXCR4 cell surface expression as well as for CXCR4 mRNA expression by RT-PCR and by Northern blotting. Neither CXCR4 protein nor mRNA could be detected in U87 cells. Primary macrophages were highly positive for cell surface CXCR4 expression after 1 day of culture; however, expression had dropped substantially by 5 days. Northern blot and RT-PCR analyses of 5-day-old primary macrophages were positive for CXCR4 mRNA but at a lower level than cell lines MOLT-4, C8166, and RD.

Table 1 summarizes the data shown in FIG. 1 and includes a survey of other cell types, including Daudi (a B-cell line), HeLa/CD4, and the CD4+ T-cell lines H9 and MT-2, as well as phytohemagglutinin- and interleukin-2-stimulated PBMCs cultured for 5 days as described previously (Simmons et al., 1996, Virology 709:8355–8360). All of these cell types stained positive for CXCR4 cell surface expression. Expression of CXCR4 by cell lines ranged from 35.5% for HeLa/CD4 to >99% for MT-2 cells. Other human cell lines, such as SCL skin and WI-38/t lung cells were negative for CXCR4 expression by 12G5 staining and for CXCR4 mRNA, like U87 glioma cells. Thus, CXCR4 is expressed widely on human hematopoietic cell types and on some nonlymphoid cell types but is absent from the surfaces of human U87 glioma, SCL skin, and WI-38/t lung cells and is only weakly expression on 5-day-old macrophages derived from blood monocytes. This pattern of CXCR4 expression correlates well with the sensitivity of these CD4+ cell types to infection by T-cell-line-passaged HIV-1 strains such as LAI and RF (Tables 1 and 2) (Chesebro, et al., 1990, supra; and Clapham et al., 1991, supra). However, HIV-2 strains (e.g., ROD) and some HIV-1 strains (e.g., the GUN-1 variant [GUN-1 var]) exhibit a broader tropism and can infect several CXCR4 cells types (e.g., U87/CD4) (Clapham et al., 1991, supra; McKnight et al., 1994, supra; McKnight et al., 1995, supra; Simmons et al., 1995, supra; and Takeuchi et al., 1991, J. Virol. 65:1710–1718).

TABLE 1

CORRELATION OF CXCR4 EXPRESSION AND INFECTION BY T-CELL-LINE-PASSAGED HIV-1

| CELL TYPE | SOURCE | Level of CXCR4 expression determined by: mRNA[a] | 12G5[b] | INFECTION BY HIV-1 LAI |
|---|---|---|---|---|
| RD/CD4 | Rhabdomyosarcoma | ++ | 93.3 | + |
| HeLa/CD4 | Cervical carcinoma | ++ | 35.5 | + |
| U87/CD4 | Glioma | − | <2 | − |
| SCL/CD4 | Skin | − | <2 | − |
| WI-38t/CD4 | Lung | − | <2 | − |
| Daudi/CD4 | B cell | ++ | 88.4 | + |
| C8166 | T cell | ++ | 72.0 | + |
| MOLT-4 | T cell | ++ | 89.5 | + |
| Sup Tl | T cell | NT[c] | 81.5 | + |
| H9 | T cell | NT | 51.4 | + |
| MT-2 | T cell | NT | 99.0 | + |
| PBMC[d] | | ++ | 27.8 | + |
| Macrophage[d] | | + | 5.2 | (−)[e] |

[a]CXCR4 mRNA was measured by RT-PCT. −, no CXCR4 expressed; +, weak CXCR4 expression; ++, high-level CXCR4 expression.
[b]Values are percentages of cells expressing CXCR4 as determined by fluorescence-activated cell sorter analysis of 12G5 staining.
[c]NT, not tested.
[d]CXCR4 expression was estimated after 5 days of culturing PBMCs or macrophages. The percentages of 12G5-positive cells are averages derived from staining 10 batches of PBMCs and 3 batches of macrophages, each from different donors.
[e](−), inefficient infection only.

TABLE 2

SUMMARY OF EXPRESSION OF CXCR4 AND SUSCEPTIBILITY TO INFECTION BY HIV-1 AND HIV-2 STRAINS

| CD4+ T-cell line or type used | Level of CXCR4 expression[a] | INFECTION BY[b]: HIV-1 STRAIN | | | | HIV-2 STRAIN | |
|---|---|---|---|---|---|---|---|
| | | LAI | RF | GUN-1wt | GUN-1var | ROD | CBL-23 |
| RD/CD4 | ++ | + | + | + | + | + | + |
| HeLa/CD4 | ++ | + | + | + | + | + | + |
| U87/CD4 | − | − | − | − | + | + | + |
| WI-38/t/CD4 | − | − | − | − | + | + | NT[c] |
| CD4+ T-cell lines | ++ | + | + | + | + | + | + |

TABLE 2-continued

SUMMARY OF EXPRESSION OF CXCR4 AND SUSCEPTIBILITY TO
INFECTION BY HIV-1 AND HIV-2 STRAINS

| CD4+ T-cell line | Level of CXCR4 | INFECTION BY[b]: | | | | | |
|---|---|---|---|---|---|---|---|
| | | HIV-1 STRAIN | | | | HIV-2 STRAIN | |
| or type used | expression[a] | LAI | RF | GUN-1wt | GUN-1var | ROD | CBL-23 |
| PBMC | ++ | + | + | + | + | + | + |
| Macrophage | + | (−)[d] | (−) | + | (−) | + | NT |

[a]−, no CXCR4 expression; +, low-level CXCR4 expression, ++, high-level CXCR4 expression.
[b]−, not susceptible; +, susceptible.
[c]NT, not tested.
[d](−), inefficient infection only.

MAb 12G5 was tested to determine if it could inhibit cell-to-cell fusion induced by a panel of HIV-1 and HIV-2 strains. The HIV-1 and HIV-2 strains tested were chosen because they show distinct tropisms for various CD4+ cell types (summarized in Table 2), but all infect CD4+ T-cell lines as well as HeLa/CD4 and RD/CD4 cells. The wild-type GUN-1 strain of HIV-1 (GUN-1 wt) is dual tropic and, unlike LAI and RF, efficiently infects primary macrophages as well as CD4+ T-cell lines (McKnight et al., 1995, supra; and Simmons et al., 1995, Virology 209:696–700). A single amino acid change in the V3 loop of GUN-1 var results in the loss of macrophage tropism but confers efficient infection of CXCR4− CD4+ U87 glioma cells (McKnight et al., 1995, supra; and Takeuchi et al., 1991, supra). Also, the HIV-2 strains used have a broader tropism for CD4+ human and nonhuman cell types (Clapham et al., 1991, supra; and McKnight et al., 1994, supra;), several of which do not express CXCR4. HIV-2 ROD/B is a variant of the prototype ROD strain (ROD/A) that can infect certain CD4− human cell types (Clapham et al., 1992, supra) with CXCR4 alone as a receptor (described herein) yet still retains the broad, CD4-dependent tropism characteristic of most T-cell-line-passaged HIV-2 isolates (McKnight et al., 1994, supra).

Uninfected target cells (e.g., RD/CD4 cells) were treated for 30 minutes with 12G5 dilutions before addition of an equal number of H9 cells chronically infected with an appropriate HIV-1 or HIV-2 strain. Cocultivations were incubated at 37° C. overnight before syncytium formation was estimated as described (Clapham et al., 1991, supra; Clapham et al., 1992, supra; and McKnight et al., 1994, supra). The data presented in Table 3 establish that 12G5 inhibited induction of cell-to-cell fusion of CXCR4+ RD/CD4 cells by all HIV-1 and HIV-2 strains tested. Thus, each of the seven HIV isolates tested uses CXCR4 as a coreceptor on RD/CD4 cells during fusion.

MAb 12G5 was then assessed to determine whether this antibody could inhibit HIV-1- and HIV-2-induced cell-to-cell fusion of CXCR4+ CD4+ T-cell lines as well as other CD4− cell types (either CXCR4+ of CXCR4−). The data presented in Table 3 establish that 12G5 failed to inhibit cell-to-cell induction of fusion by any of the seven viruses on the T-cell lines MOLT-4, Sup T1, and MT-2, although a slight but consistent reduction in syncytium formation was seen for the HIV-1 GUN-1 strains on MOLT-4 and Sup Ti cells with the highest does of 12G5 (20 μg/ml). In contrast, fusion of C8166 and CEMss T cells as well as HeLa/CD4 cells by both HIV-1 GUN-1 wt and GUN-1 var was blocked by 12G5 even though fusion by the other strains on these cell types was resistant. Likewise, HIV-2 CBL-23 was blocked for fusion on C8166 and HeLa/CD4 yet resisted 12G5 inhibition on SSCEM. 12G5 inhibition of HIV-1- and HIV-2-induced cell fusion of cell types other than RD/CD4 is therefore complex, being cell type as well as virus strain dependent. Clearly, some strains are efficiently inhibited while others are resistant.

TABLE 3

INHIBITION OF HIV-1- AND HIV-2-INDUCED SYNCYTIUM
FORMATION ON CD4+ CELL LINES BY 12G5

| | Titer of 12G5 Syncytium-Inhibiting Activity[a]: | | | | | |
|---|---|---|---|---|---|---|
| CD4− | HIV-1 STRAIN | | | | HIV-2 STRAIN | |
| T-cell line | LAI | RF | GUN-1wt | GUN-1var | ROD A/B | CBL-23 |
| RD/CD4 | 2.5 | 2.5 | 1.25 | 0.625 | 5 | 2.5 |
| HeLa/CD4 | >20[b] | >20[b] | 5 | 5 | >20 | 5 |
| C8166 | >20 | >20 | 2.5 | 2.5 | >20 | 2.5 |
| MOLT 4 | >20 | >20 | >20[b] | >20[b] | >20 | >20 |
| Sup Tl | >20 | >20 | >20[b] | >20 | >20 | >20 |
| MT-2 | >20 | >20 | >20 | >20 | >20 | >20 |
| U87/CD4/ CXCR4 | >20 | | | | | |

[a]Antibody titers were estimated as the highest concentration of 12G5 (μg/ml) that inhibited >95% syncytium formation; i.e., >20 means there was no inhibition by 12G5 up to a concentration of 20 μg/ml, whereas 1.25 means that 12G5 blocked >95% of syncytium formation at 1.25 μg/ml but lower concentrations inhibited less or not at all. Unless otherwise noted,the titers shown refer to >95% syncytium inhibition.
[b]Consistent reduction of up to 50% syncytium formation at 20 μg/ml was seen.

Figure 2A:
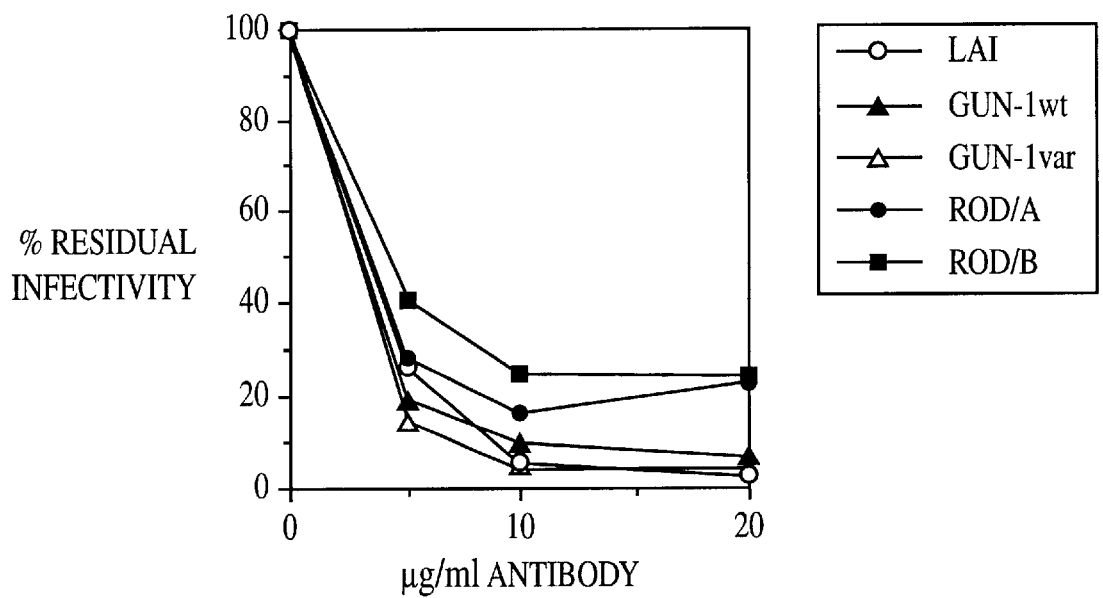
FIG. 2A is a graph depicting 12G5-mediated inhibition of cell-free infectivity of RD/CD4 cells.
Figure 2B:
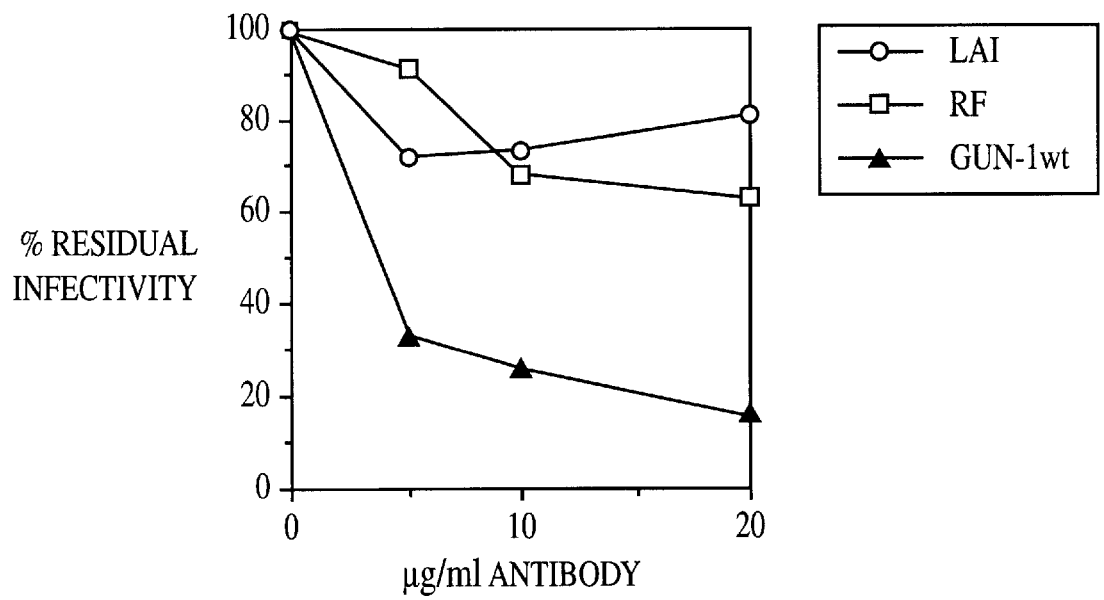
FIG. 2B is a graph depicting 12G5-mediated inhibition of cell-free infectivity of HeLa/CD4 cells.

MAb 12G5 inhibition of infection of cells by cell-free virus was assessed as follows. RD/CD4 or HeLa/CD4 were seeded at $2 \times 10^4$ cells per well in 24-well trays 2 days before infection. Cells were treated for 30 minutes with 100 μl of appropriate 12G5 antibody dilutions. Virus supernatant (100 μl) containing between 50 and 100 focus-forming units was added, and the cultures were incubated for a further 90 minutes. Inocula were then removed, and cells were washed twice before the addition of 1 ml of growth medium and incubation for 4 days. Foci of infection were detected by immunostaining as previously described (Clapham et al., 1992, supra). The data presented in FIGS. 2A and B demonstrate that the pattern of 12G5 inhibition of infectivity for RD/CD4 cells and HeLa/CD4 cells exactly followed that observed for inhibition of cell fusion. The infectivity of all strains tested on RD/CD4 cells was inhibited by 12G5. However, on HeLa/CD4 cells, GUN-1 wt was blocked by 12G5 whereas only slight inhibition of the LAI and RF strains was observed.

The simplest explanation for these results is that certain HIV strains can use coreceptors other then CXCR4 on some cell types (and particularly on CD4$^+$ T-cell lines) and are therefore not substantially inhibited by 12G5. For the T-cell-line-adapted strains used in this study, CXCR4 must be the only coreceptor choice on CXCR4$^+$ RD cells, so the anti-CXCR4 MAb 12G5 inhibits infection. On most CXCR4$^+$ CD4$^+$ T-cell lines, 12G5 failed to inhibit HIV-1 and HIV-2 fusion, suggesting the presence of alternative coreceptors. This interpretation is supported by the observation that certain HIV-1 (GUN-1 wt and GUN-1 var) and HIV-2 strains can infect at least some CXCR4-CD4$^+$ cell types (Table 2) and therefore must use alternative coreceptors for entry into these cells. Thus, as reported already by Choe et al. (1996, Cell 85:1135–1148) and Doranz et al. (1996, Cell 85:1149–1158), at least some HIV strains can choose between compatible alternative coreceptors for CD4-dependent entry. Furthermore, it has recently been shown that several primary dual-tropic HIV-1 isolates (as well as GUN-1 wt) infected cat CCC cells expressing human CD4 as long as either CXCR4 or CCR5 was present, while a subset of the primary strains could use CCR3, CCR5, or CXCR4 (Simmons et al., 1996, supra). Yet, LAI- and RF-induced fusion of C8166, as well as GUN-1 wt-induced fusion of MOLT-4 cells, which are resistant to 12G5 inhibition, also resisted inhibition by a combination of 12G5 (20 μg/ml) and RANTES (200 ng/ml). RANTES binds to a number of CC chemokine receptors (Chaudhuri et al., 1994, J. Biol. Chem. 269:7835–7838; Neote et al., 1993, Cell 72:415–425; Power et al., 1995, J. Biol. Chem. 270:19495–19500; Samson et al., 1996, Biochemistry 35:3362–3367), including CCR5, a coreceptor for NSI macrophage-tropic HIV-1 strains (Alkhatib et al., 1996, Science 272:1955–1958; Deng et al., 1996, Nature 381:661–666; Dragic et al., 1996, Nature 381:667–673; Weiss et al., 1996, Nature 381:647–648) and inhibits PBMC infection by NSI macrophage-tropic strains (Cocchi et al., 1995, Science 270:1811–1815; Deng et al., 1996, supra; Dragic et al., 1996, supra). Thus, if alternative coreceptors present on CD4$^+$ T-cell lines are exploited by the virus strains used here, it is unlikely that they are receptors for RANTES.

The data suggest that the processing presentation of CXCR4 is different on different cell types, enabling at least some HIV strains to evade 12G5 inhibition. Perhaps on some cell types, other cell surface molecules interact with CXCR4, influencing HIV recognition of the coreceptor. Indeed, expression of CXCR4 on CD4$^+$ U87 cells (Deng et al., 1996, supra) confers sensitivity to LAI fusion which is resistant to 12G5 inhibition (Table 3). Thus, at least for this situation, in which recombinant CXCR4 should be the only coreceptor available for LAI on U87/CD4 cells, 12G5 fails to block fusion. Furthermore, although 12G5 failed to block LAI infection of HeLa/CD4 cells, others have shown that the CXCR4 ligand SDF-1 does block infection (Bleul et al., 1996, Nature 282:829–833; Oberlin et al., 1996, Nature 382:833–835). Assuming that SDF-1 is specific for CXCR4, this observation implies that CXCR4 is the only coreceptor available for LAI on HeLa/CD4 cells. Thus, although 12G5 binds to CXCR4 on both RD/CD4 and HeLa/CD4 cells, differences in the processing or presentation of CXCR4 must enable LAI to resist 12G5 inhibition on HeLa/CD4 cells but not on RD/CD4 cells.

The existence of different forms of CXCR4 presentation on different cell types may explain the cell-type-dependent inhibition of HIV strains shown here but does not resolve why inhibition on some cell types (e.g., C8166 and HeLa/CD4) was also virus strain dependent. It is thus likely that different strains interact differently with CXCR4 to trigger fusion. Although the natures of the different interactions are currently unknown, this hypothesis is supported by our recent observation that deletions at the N terminus of CXCR4 have different effects depending on the HIV strain tested.

In summary, the data establish that HIV-induced infection and cell-to-cell fusion is inhibited by a novel MAb (12G5) to CXCR4, the coreceptor for T-cell-line-adapted HIV strains. 12G5 inhibition was cell type and virus strain dependent. Variations in processing or presentation of CXCR4 or expression of alternative coreceptors meant that 12G5 failed to block most HIV-1 and HIV-2 strains on CD4$^+$ T-cell lines. These results indicate that the designing of therapeutic molecules to intervene in HIV and coreceptor interaction will not be straightforward and suggest that resistant escape mutants will emerge.

EXAMPLE 2

CD4-Independent Infection by HIV-2 is Mediated by Fusin/CXCR4

The Experimental Procedures used in Example 2 are now described. Cells CD4-positive human T lymphoid cell lines, Sup-T1, Hut-78, H9, CEM, Molt4-clone8, and the TxB cell hybrid line, CEMx174, have been described previously (Hoxie et al., 1986, Science 234:1123–1127; Hoxie et al., 1988, J. Virol. 62:2557–2568; LaBranche et al., 1994, J. Virol. 68:5509–5522). CD4-negative T lymphoid lines HSB and CEMss4$^-$ are described (Weiner et al., 1991, Pathobiol. 59:361–371 and Nara et al., 1987, AIDS Res. and Hum. Retroviruses 3:283–202, respectively) and BC7 was derived from Sup-T1 cells, as described in Table 4. Human B cell lines, Nalm6, KM3.79, and REH are described (McKnight et al., 1995, J. Virol.69:3167–3170; McKnight et al., 1996, J. Virol. 70:4598–4606) HeLa, RD, and Daudi cells have been described previously (Clapham et al., 1991, supra 5; Clapham et al., 1992, supra). 293T and CCCS-L-cells are well known in the art and were provided by Michael Malim (University of Pennsylvania); QT6–5 Japanese quail fibrosarcoma cells are also well known in the art and were provided by Paul Bates (University of Pennsylvania), and murine myeloma SP2 cells and the W6/32 hybridoma cell line were obtained form the American Type Culture collection. U87 cells stably expressing recombinant Fusin, CCR1, CD4 were derived as described previously (Deng et al., 1996, supra). Murine NIH 3T3 cells expressing either Fusin alone or Fusin and human CD4 are described (Deng et al., 1996, supra). Chinese hamster ovary cells (CHO-K1) expressing HA-tagged or untagged human chemokine receptors were derived using cDNAs derived by RT-PCR and cloned into pcDNA1neo for expression in mammalian cells (Power et al., 1996, Trends Pharmacol. Sci. 17:209–213). Stable CHO lines expressing the chemokine receptors were derived by screening for reactivity to the anti-HA MAb, 12CA5. The receptor selectivity of the HA-tagged receptor lines was tested by radioligand binding assays using membranes purified from the respective cells. No significant differences in ligand binding properties were seen between tagged and nontagged receptors.

Viruses An uncloned viral stock of HIV-2/NIH-z was used and HIV-2/vcp was derived from HIV-2/NIH-z (Zagury et al., 1988, Proc. Natl. Acad. Sci. USA 85:5941–5945) by passaging virus first onto CP-MAC infected Sup-T1 cells that had completely down-regulated their surface expression of CD4 (LaBranche et al., 1994, supra), and then onto BC7 cells. Sequence analysis of the HIV-2/vcp env gene amplified from genomic DNA showed no evidence of recombination in env with CP-MAC. CP-MAC was derived as previously described from the SIVmac molecular clone, BK28 (LaBranche et al., 1994, supra). Additional variants of HIV-2 described for their ability to infect CD4-negative cells included HIV-2/CBL-23, HIV-2/Rod-A, and HIV-2/Rod-B (Clapham et al., 1992, supra).

Constructs The HIV-2/vcp env gene was PCR amplified from genomic DNA from HIV-2/vcp-infected HSB cells using the primer pair 5'-GGCTCATCCGGTCGA CGAATCAGACAAGTGAGTATGAAGGGTAGTAAG-3' [SEQ ID NO:5], and 5'-CTGCTGATATCGCTGTCCCTC ACAGGAGGGCGAG-3' [SEQ ID NO:6], and was cloned into the eukaryotic expression vector pCR3.1 (Invitrogen). The BH8 env clone is described (Ratner et al., 1987, AIDS Res. and Hum. Retroviruses 3:57–69). Fusin and CD4 were expressed as previously described (Berson et al., 1996, J. Virol. 70:6288–6295; Doranz et al., 1996, supra). The IL8 receptor clone is described (Ratner et al., 1987, AIDS Res. and Hum. Retroviruses 3:57–69).

Antibodies 12G5 was produced by inoculating Balb/c mice with $10^7$ living CP-MAC-infected Sup-T1 cells intraperitoneally for 3 weekly injections, and fusion protocols were performed as described (Brass et al., 1994, J. Biol. Chem. 269:2943–2952). Hybridomas were screened in 96-well plates for the ability to inhibit CP-MAC-induced syncytium induction on Sup-T1 cells and were then cloned by limiting dilution. Antibody was purified from ascites using HiTrap Protein G (Pharmacia Biotech). The anti-CD4 MAB #19 was produced using a similar protocol in which the immunizing cell type was uninfected Sup-T1 cells. Specificity of this antibody for CD4 was determined by its ability to detect the 55 kDa CD4 protein by Western blot from lysates of CD4-positive cells. The anti-CD4 MAbs OKT4A and OKT4 were purchased from Ortho Pharmaceuticals, and 12 CA5 was purchased from Boehringer-Mannheim. D47 is an $IgG_{2a}$ MAB reactive with the HIV-1/LA1 gp 120. Rabbit anti-human CD4 serum was used in these experiments.

Viral Infection and Neutralization Assays Virus infection assays on lymphoid cell lines and U87 cells expressing recombinant Fusin or CD4 were performed by inoculating cultures with 1000 $TCID_{50}$ units of either HIV-1/LA1 or HIV-2/vcp. Input virus was washed out after 24 hours and cultures were monitored for infection by serial determinations of reverse transcriptase activity and visual inspection for syncytium formation. For neutralization assays, target cells were preincubated with varying concentrations of either 12G5 or anti-CD4 MAbs for 30 minutes at 37° C. followed by the addition of 100 $TCID_{50}$ units of virus, as titered on each target cell. Input virus was removed after 24 hours and cultures were monitored for infection as described herein. Cells were maintained in the presence of antibody for the duration of the experiment.

Cell Fusion Assays Syncytium induction assays were performed as previously described (LaBranche et al., 1994, supra). In brief, HIV- or SIV-infected cells were added to target cells growing as suspension cultures or adherent cells at a ratio of approximately 1 to 5. After 24 or 48 hours, samples were either inspected visually by phase contrast microscopy or fixed and stained with Wright stain and 10% Giemsa. In selected experiments, MAbs were preincubated with target cells for 30 min at 37° C. For experiments involving HIV-2/Rod-A or HIV-2/CBL-23, which require priming with soluble sCD4 to infect CD4-negative cells, H9 cells chronically infected with these viruses were preincubated with 5 µg/ml of soluble CD4 prior to cocultivation with target cells as described (Clapham et al., 1992, supra).

Cell fusion induced by cloned env genes was quantitated using a luciferase gene reporter assay (Doranz et al., supra). In brief, HeLa effector cells were transfected with HIV env-containing constructs and infected with recombinant vaccinia virus encoding the T7 polymerase gene. Target cells were quail QT6 cells that were transfected with a plasmid containing the luciferase gene driven by a T7 promoter (Promega). Selected target cells were also transfected with pT4 which constitutively expresses CD4 from the CMV promoter. Effectors and target cells were mixed and allowed to fuse for 8 hours. Cells were then washed with PBS and lysed in 150 µl reporter lysis buffer (Promega) and assayed for luciferase activity according to the instructions of the manufacturer.

Flow Cytometry Surface expression of cell surface antigens was performed by FACS analysis using a Becton-Dickinson FACScan flow cytometer (LaBranche et al., 1994, supra). For experiments involving adherent cells, cells were dislodged from plates by treatment with PBS/1 mM EDTA. All HIV- or SIV-infected cell samples were fixed at 4° C. for 24 hours in 4% paraformaldehyde prior to analysis.

Iodinated Antibody Binding Assays Binding assays with iodinated 12G5 and iodinated 12CA5 were performed essentially as described (Pelchen-Matthews et al., 1989, EMBO J. 8:3641–3649). 12G5 and 12CA5 were labeled with $^{125}I$ using Bolton and Hunter reagent (Amersham, U.K.) to a specific activity of 390 and 550 Ci per mmole, respectively. Cells were cultured in 24-well plates and were incubated with 1 nM $^{125}I$-12G5 and 2 nM 12CA5 for 2–4 hr at 4° C., then washed and the amount of bound antibody was determined by γ-counting. Background levels of binding were determined by performing assays in the presence of 100 nM unlabeled antibody.

Immunofluorescence Microscopy CHO cells either stably or transiently expressing Fusin or other chemokine receptors were cultured on glass coverslips and fixed in 3% paraformaldehyde. Cells were washed, quenched in 50 mM $NH_4$ and 0.2% fetal calf serum, and stained with the respective antibodies for 1 hour at room temperature. Cells were then washed, stained with TRITC-conjugated goat anti-mouse 1 gG for 1 hour, washed again and mounted in Moviol. Cells were photographed using a Nikon Optiphot-2 microscope equipped with an MRC Bio-Rad 1024 laser scanning attachment.

The Results of the experiments presented in Example 2 are now described.

Derivation of an HIV-2 Variant That Infects Cells in the Absence of CD4

Figure 3A:
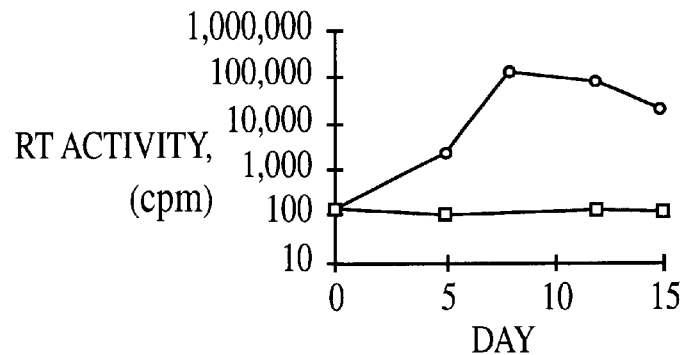
FIG. 3A is a series of graphs depicting infection of CD4 negative cells with HIV-2/vcp. The cell lines indicated in the panels were inoculated with cell-free HIV-2/vcp or HIV-1/LAI and were monitored for reverse transcriptase (RT) activity in culture supernatant at the indicated time points. Input virus was removed after 24 hours by washing. Except for Sup-T1, all cell lines were CD4-negative as determined by FACS analysis using a panel of anti-CD4 MAbs and/or by western blot using an anti-CD4 serum.
Figure 3B:
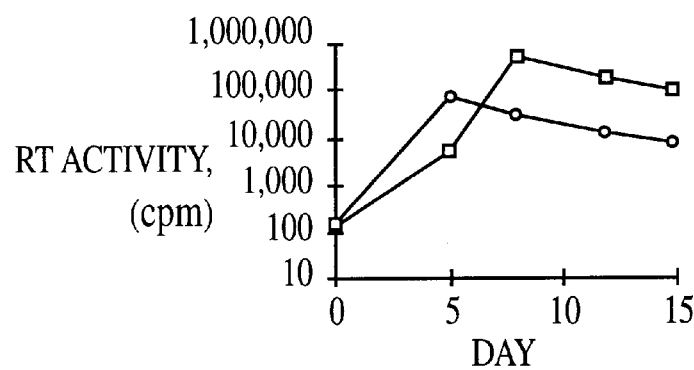
FIG. 3B is a graph depicting the failure of an anti-CD4 MAb to inhibit HIV-2/vcp infection of a CD4-negative cell line. BC7 or Sup-T1 cells were inoculated with either HIV-2/vcp or HIV-1I/LAI, respectively, in the presence or absence of anti-CD4 MAb #19. Input virus was removed after 24 hours by washing and cells were maintained in the presence of anti-CD4 MAb for 8 days at which time RT activity was determined. Similar results were seen using OKT4A, another anti-CD4 MAb.
Figure 3B:
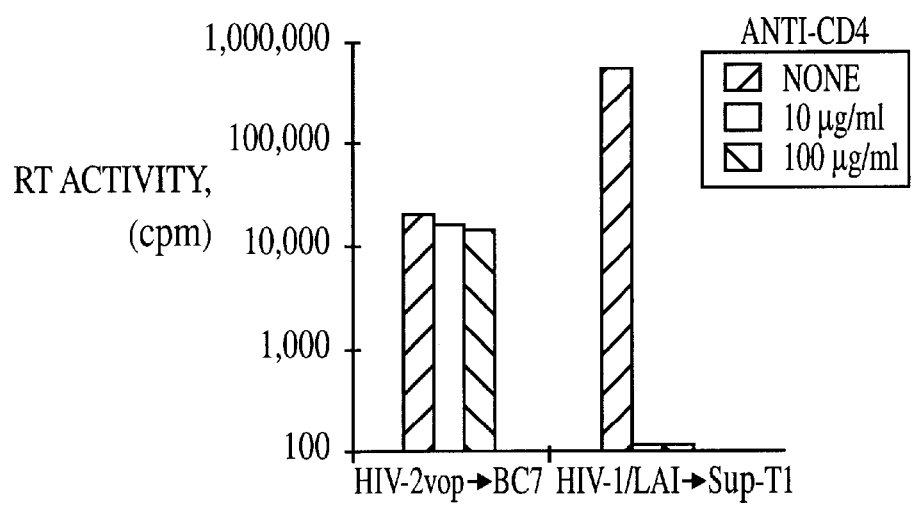

To study receptors involved in CD4-independent infection, a biological variant of HIV-2, termed HIV-2/vcp, was derived from the HIV-2/NIH-z isolate (Zagury et al., 1988, supra) (see FIG. 3). HIV-2/vcp was shown to infect a number of CD4-negative lymphoid cell lines of T-(BC7, HSB, CEMss4-) and B-(Daudi and Na1m6) cell origin (FIG. 3A) as well as the nonlymphoid rhabdomyosarcoma line RD. As expected, no infection was seen when these cell types were inoculated with the T cell line-tropic isolate HIV-1/LA1 (FIG. 3A). In addition, anti-CD4 MAbs were unable to inhibit infection of BC7 (FIG. 3B), Daudi or Na1m6 cells, or cell-to-cell fusion between HIV-2/vcp-infected cells and uninfected BC7 cells (FIG. 3C). Similar to other HIV-2 isolates that can infect CD4-negative cells (Clapham et al., 1992, supra), HIV-2/vcp infected the majority of these cell types with extensive cell fusion and killing, indicating the highly efficient use of one or more alternative receptors.

12G5. a Monoclonal Antibody That Inhibits CD4-Independent Infection by HIV-2

In an effort to analyze interactions between cellular molecules and viral envelope glycoproteins, the anti-cellular MAB, termed 12G5, was derived that was able to inhibit syncytium induction by HIV-2/vcp on CD4-negative cell lines (see the Experimental Procedures section of Example 2 and FIG. 4A). This MAB also inhibited syncytium induction by CP-MAC, a biological variant of SIVmac that has been shown to be highly infectious and fusogenic for Sup-T1 cells in a CD4-dependent manner (LaBranche et al., 1994, supra) (FIG. 4A). 12G5 was shown by FACS analysis to react with several CD4-positive and -negative human hematopoietic cell lines (Table 1) and with unfractionated human peripheral blood lymphocytes. Reactivity was also seen with some nonhematopoietic human cell lines including HeLa (cervical carcinoma) and RD (rhabdomyosarcoma), but not HOS (osteosarcoma) or U87 (glial) cells (Table 4). No reactivity was observed in the case of the murine myeloma line, SP2, or the other nonhuman cell lines shown in Table 4.

TABLE 4

REACTIVITY OF 12G5 MONOCLONAL ANTIBODY WITH DIFFERENT CELL LINES

| CELL LINE | SPECIES/ORIGIN | 12G5 REACTIVITY | CD4 |
|---|---|---|---|
| SupT1 | Human/T-cell | + | + |
| Hut-78 | Human/T-cell | + | + |
| CEMss | Human/T-cell | + | + |
| Molt4 clone 8 | Human/T-cell | + | + |
| HSB | Human/T-cell | + | − |
| BC7 | Human/T-cell | + | − |
| CEMss4− | Human/T-cell | + | − |
| CEMx174 | Human/TxB hybrid | + | + |
| Daudi | Human/B-Cell | + | − |
| Nalm6 | Human/B-Cell | + | − |
| KM3.79 | Human/B-Cell | + | − |
| REH | Human/B-Cell | + | − |
| RD | Human/rhabdomyosarcoma | + | − |
| HeLa | Human/cervical carcinoma | + | − |
| HOS | Human/osteosarcoma | − | − |
| 293T | Human/embryonal kidney | − | − |
| U87 | Human/astrocyte, glial | − | − |
| CCCS+L- | Feline/kidney | − | − |
| QT6-5 | Quail/fibrosarcoma | − | − |
| CHO | Hamster/ovary | − | − |
| SP2 | Murine/B-cell | − | − |

Cells were stained for FACS analysis (Hoxie et al., 1986, Science 234:1123–1127) with 10–15 μg/ml of 12G5, an amount sufficient to saturate the binding sites on Sup-T1 and BC7 cells. Reactivity was compared to an $IgG_{2a}$ control MAB isotype matched to 12G5 (Earl et al., 1994, J. Virol. 68:3015–3026). A panel of anti-CD4 MAbs was used to evaluate CD4 expression including OKT4, OKT4A, and #19, a competitive inhibitor of Leu3a (Endres et al., 1996, Cell 87:745–756). "+" indicates reactivity ≧3 fold that of the negative control MAB. CEMss4− cells are a CD4-negative variant of CEMss generated by serially panning with an anti-CD4 MAB, sorting for CD4-negative cells and cloning by limiting dilution. BC7 cells were cloned by limiting dilution from a culture of Sup-T1 cells chronically infected by HIV-1/NL4-3. BC7 cells exhibit no detectable HIV-1, as determined by soluble p24 production, coculturing with susceptible cell lines, and PCR of genomic DNA with primers specific for the HIV-1 LTR, gag and env. Lysates of BC7 and CEMss4− cells exhibit no detectable CD4 protein by western blot using a rabbit anti-CD4 antiserum. HSB is a CD4-negative and CD8-positive human T-cell line (Weiner et al., 1991, Pathobiol. 59:361–371).

In addition to inhibiting cell fusion, 1 2G5 also neutralized infection by HIV-2/vcp and CP-MAC when preincubated with appropriate target cells. CP-MAC infection of Sup-T1 cells was readily inhibited by antibody concentrations of 1 μg/ml while somewhat higher concentrations (5–20 μg/ml) were required to inhibit HIV-2/vcp infection of CD4-negative lines including BC7, Na1m6, and Daudi (FIG. 4B). Infection of these cell types was not inhibited by $IgG_{2a}$ monoclonal antibodies that were isotype matched for 12G5. Although 12G5 frequently caused cell clumping (FIG. 4A), no inhibitory effects were seen on cell growth and no toxic effects were apparent when cells were cultured in antibody concentrations as high as 50 μg/ml.

12G5 also inhibited two other HIV-2 isolates, HIV-2/Rod-A and HIV-2/Rod-B, that have been shown to induce fusion on CD4-negative cell lines including Daudi and RD (Clapham et al., 1992, supra). HIV-2/Rod-A infectivity has been shown to be enhanced by preincubation with soluble CD4 (sCD4) while HIV-2/Rod-B induces syncytia on these CD4-negative cells without sCD4. As shown in Table 5, 12G5 inhibited cell fusion at concentrations >5 μg/ml when H9 cells chronically infected by HIV-2/Rod-A or /Rod-B were cultured in the presence or absence of sCD4, respectively. Inhibition was also observed in the case of another HIV-2 isolate, HIV-2/CBL-23 that induces syncytia on RD cells following preincubation with sCD4 (Table 5) Clapharn et al., 1992). Therefore, in addition to its anti-viral effects on CP-MAC and HIV-2/vcp, 12G5 inhibited infection and/or cell fusion by two other genetically distinct isolates of HIV-2 on CD4-negative target cells.

TABLE 5

INHIBITION OF HIV-2 SYNCYTIUM INDUCTION BY 12G5 ON CD4-NEGATIVE CELL LINES[1]

| HIV-2 INFECTED CELL[2] | | TARGET CELL[3] | |
|---|---|---|---|
| CELL | VIRUS | RD | DAUDI |
| H9 | HIV-2 Rod-B | 2.5 | 5.0 |
| H9 | HIV-2 Rod-A plus sCD4 | 5.0 | 5.0 |
| H9 | HIV-2 CBL-23 plus SCD4 | 5.0 | 5.0 |

[1]CD4-negative RD or Daudi cells were treated for 30 minutes with varying concentrations of 12G5 MAB before adding an equal number of H9 cells chronically infected with the HIV-2 isolate indicated. Cultures were maintained at 37° C. overnight before counting the number of syncytia.
[2]Where indicated, infected cells were preincubated with sCD5 (1 μg/ml) at 37° C. for 60 minutes.
[3]Numbers indicate the minimum antibody concentration (μg/ml) that inhibited syncytium formation by >95%.

MAB 12G5 Reacts with Fusin

Although 12G5 was shown to react with the cell surface by FACS, efforts to immunoprecipitate or immunoblot the antigen under a variety of conditions were unsuccessful. MAB 12G5 was examined for reactivity to Fusin. U87 cells that stably expressed either Fusin or the CC-chemokine receptor, CCR1, were derived and evaluated by FACS for 12G5 binding. Remarkably, 12G5 reacted strongly with U87 cells that expressed Fusin while only background staining was detected on U87 cells that expressed CCR1 or cells transduced with the control vector alone (FIG. 5A). Similar results were seen for human 293T cells in which Fusin was transiently expressed during transfection of cells by a plasmid encoding this protein.

To determine if 12G5 reacted with other chemokine receptor family members, a panel of CHO cell lines was used that stably expressed either Fusin, CC-chemokine receptors (CCR1, CCR2b, CCR3, CCR4, or CCR5), or CXC-chemokine receptors (IL8R-A or IL8R-B). The recombinant receptors in these CHO lines were expressed as either untagged or tagged proteins wherein the amino terminus was tagged with the influenza hemagglutinin (HA) epitope. Surface binding assays were performed using $^{125}$I-labeled 12G5 and showed specific binding only to cells that expressed Fusin (FIG. 5B). Scatchard analysis of 12G5 binding on CHO cells expressing HA-tagged Fusin or to RD or BC7 cells showed approximately $1^6$, $4 \times 10^5$, and $5 \times 10^4$ antibody molecules bound per cell, respectively, with a $K_d$s of 1–5 nM.

Analysis of Fusin-expressing CHO cells was also performed by immunofluorescence confocal microscopy of intact cells. As shown in FIG. 5C, staining was observed on cells expressing HA-tagged Fusin while no reactivity was seen on cells expressing HA-tagged IL8R-B receptors. Expression of each protein could be detected using an HA-specific MAB, and no staining was observed when an anti-CD4 MAB was used as a control (FIG. 5C). Similar negative results were observed when CHO cells expressing other chemokine receptors including, IL8R-A, CCR1, CCR2b, CCR3, CCR4, and CCR5 were stained with 12G5. Intracellular Fusin was also detectable using 12G5 on cells permeabilized with saponin. Therefore, 12G5 bound specifically to both human and nonhuman cells that expressed recombinant Fusin, strongly suggesting that this antibody reacts specifically with the human Fusin protein.

Fusin Serves as an Alternative Receptor for HIV-2/vcp in the Absence of CD4

Because 12G5 was able to inhibit CD4-independent infection by some HIV-2 isolates, the above findings suggested that Fusin was functioning as an alternative receptor for these viruses. In order to test this hypothesis, U87 cells that stably expressed either recombinant Fusin or CD4 were valuated in coculture assays for their ability to form syncytia with HIV-2/vcp-infected cells. As previously noted, U87 cells exhibited no reactivity with 12G5 by FACS analysis (Table 4) and have no detectable Fusin mRNA (Feng et al., 1996, supra; McKnight et al., 1994, supra). As shown (FIG. 6A), when Fusin-expressing U87 cells were cocultured with HIV-2/vcp-infected BC7 cells, extensive cell fusion was observed. Preincubating cells with 12G5 (10 μg/ml) completely abolished syncytium formation. No cell fusion was observed when similar cocultures were performed with nontransduced U87 cells or with U87 cells that expressed only recombinant CD4 (FIG. 6A). Similar results were also observed in the case of murine NIH 3T3 fibroblast cells that stably expressed Fusin in the absence of CD4.

Experiments were performed to determine if recombinant Fusin could mediate productive infection by cell-free HIV-2/vcp. Control U87 cells or U87 cells that stably expressed either Fusin or CD4 were incubated with HIV-2/vcp and monitored for infection by serial determination of reverse transcriptase activity in the culture supernatant. As shown (FIG. 6B), virus replication was detectable only on U87 cells that expressed Fusin and was associated with extensive cytopathic effects including syncytium formation and cell killing.

In order to evaluate the function of the HIV-2/vcp envelope glycoprotein in the absence of other viral gene products, the HIV-2/vcp env gene was PCR amplified from genomic DNA, cloned and expressed in HeLa cells, and cell-to-cell fusion was quantitated as previously described using a luciferase gene reporter assay (Doranz et al., 1996, supra). Quail QT6 target cells were transfected with a luciferase reporter gene and either Fusin alone or Fusin with CD4. As shown (FIG. 7), the HIV-2/vcp envelope glycoprotein fused with Fusin-expressing target cells in the presence and absence of CD4. In contrast a comparably expressed BH8 envelope glycoprotein derived from a T cell line-tropic HIV-1 induced fusion on Fusin-expressing cells only in the presence of CD4. No fusion was seen when HIV-2/vcp env-expressing cells were cultured with QT6 cells transfected with the IL8R-B receptor or the expression vector alone (FIG. 7). Taken together, these results establish that Fusin can serve as an alternative receptor for some isolates of HIV-2 in the absence of CD4 on human as well as nonhuman target cells. These findings also demonstrate that in the case of HIV-2/vcp, CD4 alone is not sufficient to permit viral entry and indicate that the utilization of Fusin is an obligatory step for this virus during infection.

Down-Regulation of Surface Fusin by HIV-2/vcp Infection

Cellular receptors for enveloped viruses are characteristically down-regulated from the cell surface following productive infection, rendering infected cells resistant to superinfection by viruses that utilize the same receptor (Weiss, 1993, In the Retroviridae, J. A. Levy, ed., New York, Plenum Press, pp. 1–108). Indeed, the observation that CD4 was selectively down-regulated on HIV-1 infected cells provided the initial evidence that CD4 was a receptor for this virus (McDougal et al., 1986, Science 231:382–385). Down-regulation of CD4 and other viral receptors by envelope glycoproteins has been attributed to the formation of intracellular complexes between envelope molecules and the cellular receptors and/or to the blocking of binding sites on receptors that are expressed on the cell surface (Hoxie et al., 1986, supra; Crise et al., 1990, J. Virol. 64:5585–5593; Schneider-Schaulies et al., 1995, Proc. Natl. Acad. Sci. USA 92:3943–3947). Given the evidence that Fusin was serving as a primary receptor for HIV-2/vcp, MAB 12G5 was used to determine if this molecule was down-regulated during HIV-2/vcp infection.

BC7, Daudi, and Na1m6 cells that were either uninfected or chronically infected by HIV-2/vcp were evaluated for Fusin expression by FACS analysis using 12G5. As shown in FIG. 8, in HIV-2/vcp-infected cells, 12G5 binding was reduced 98%, 79% and 87% compared to uninfected cells. In contrast, no reduction in expression of HLA class I or transferrin receptors was observed using MAbs specific for these proteins. Thus, in the case of several CD4-negative lymphoid cells, HIV-2/vcp infection produced a marked and selective reduction in 12G5 binding. Although this experiment could not distinguish between the loss of surface Fusin and blocking of the 12G5 epitope, this result is entirely consistent with other evidence noted above that Fusin is serving as a primary viral receptor for HIV-2/vcp. As expected, CD4 was down-regulated 95% and 98% on HIV-2/vcp and CP-MAC-infected Sup-T1 cells, respectively. Interestingly, although Fusin was also down-regulated 75% on HIV-2/vcp-infected Sup-T1 cells, no reduction in 12G5 reactivity was observed on Sup-T1 cells that were infected by CP-MAC (FIG. 8) or HIV-1/LAI. Because CP-MAC (LaBranche et al, 1994, supra) and HIV-1/LAI are dependent on CD4, this finding indicates that Fusin down-regulation occurs when it is utilized as a primary receptor in the absence of CD4 but not as a CD4-associated coreceptor.

The disclosures of each and every patent, patent application and publication are hereby incorporated herein by reference.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalents.

What is claimed is:

1. An antibody which binds to a cellular chemokine receptor protein essential for immunodeficiency virus entry into a cell wherein said chemokine receptor protein is not CD4.

2. The antibody of claim 1, wherein said immunodeficiency virus is selected from the group consisting of HIV-1, HIV-2 and SIV.

3. The antibody of claim 1, wherein said protein is a cellular protein which is an HIV receptor protein.

4. The antibody of claim 1, wherein said protein is a cellular cofactor for a cellular protein which is a HIV receptor protein.

5. The antibody of claim 4, wherein said protein is selected from the group consisting of CXCR4 and CCR5.

6. The antibody of claim 5, wherein said protein is CXCR4.

7. The antibody of claim 1, wherein said antibody is selected from the group consisting of a monoclonal antibody and a synthetic antibody.

8. The antibody of claim 7, wherein said antibody is a monoclonal antibody.

9. The antibody of claim 8, wherein said antibody is MAB 12G5.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
         (A) LENGTH: 27 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

TAGATATCTT ACCATGGAGG GGATCAG                                              27

(2) INFORMATION FOR SEQ ID NO:2:

(i) SEQUENCE CHARACTERISTICS:
         (A) LENGTH: 28 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

TAGCGGCGCT TAGTGGAGTG AAAACTTG                                             28

(2) INFORMATION FOR SEQ ID NO:3:

(i) SEQUENCE CHARACTERISTICS:
         (A) LENGTH: 21 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

TGGATATTGC CATCAATGAC C                                                    21

(2) INFORMATION FOR SEQ ID NO:4:

(i) SEQUENCE CHARACTERISTICS:
         (A) LENGTH: 22 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

```
GATGGCATGG ACTGTGGTCA TG                                                          22

(2) INFORMATION FOR SEQ ID NO:5:

(i) SEQUENCE CHARACTERISTICS:
        (A) LENGTH: 48 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

GGCTCATCCG GTCGACGAAT CAGACAAGTG AGTATGAAGG GTAGTAAG                               48

(2) INFORMATION FOR SEQ ID NO:6:

(i) SEQUENCE CHARACTERISTICS:
        (A) LENGTH: 34 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

CTGCTGATAT CGCTGTCCCT CACAGGAGGG CGAG                                             34
```